United States Patent
Polichar et al.

(10) Patent No.: US 6,178,224 B1
(45) Date of Patent: Jan. 23, 2001

(54) ENHANCED X-RAY CONVERTER SCREEN FOR X-RAY RADIOSCOPIC SYSTEMS

(75) Inventors: Raulf M. Polichar; Richard C. Schirato; Janis Baltgalvis, all of San Diego, CA (US)

(73) Assignee: Science Applications International Corporation, San Diego, CA (US)

(*) Notice: Under 35 U.S.C. 154(b), the term of this patent shall be extended for 0 days.

(21) Appl. No.: 09/225,885

(22) Filed: Jan. 5, 1999

Related U.S. Application Data

(60) Continuation-in-part of application No. 09/076,604, filed on May 11, 1998, now Pat. No. 5,909,478, which is a division of application No. 08/773,483, filed on Dec. 23, 1996, now Pat. No. 5,828,726, which is a continuation of application No. 08/494,251, filed on Jun. 23, 1995, now Pat. No. 5,608,774.

(51) Int. Cl.$^7$ .................................................. H05G 1/64
(52) U.S. Cl. ..................... 378/98.2; 378/98.3; 250/368
(58) Field of Search ................................ 378/98.2, 98.3, 378/98, 62; 250/361 R, 363.01, 368

(56) References Cited

U.S. PATENT DOCUMENTS

| | | | |
|---|---|---|---|
| 4,383,327 | 5/1983 | Kruger | 378/19 |
| 4,593,337 | 6/1986 | Mouyen | 378/98.8 |
| 4,612,660 | 9/1986 | Huang | 378/44 |
| 5,008,547 | * 4/1991 | Molteni et al. | 250/368 |
| 5,127,032 | 6/1992 | Lam et al. | 378/98.3 X |
| 5,235,191 | 8/1993 | Miller | 378/98.3 X |

(List continued on next page.)

FOREIGN PATENT DOCUMENTS 0429977    11/1990    (EP) .

OTHER PUBLICATIONS

Street, et al., "Charge–Coupled Devices and Solid State Optical Sensors IV", *SPIE*, 2172:144–154 (Feb. 7–8, 1994).
Street, et al., "Amorphous Silicon Arrays Develop a Medical Image", *IEEE*, pp: 38–42 (Jul. 1993).

(List continued on next page.)

*Primary Examiner*—David P. Porta
(74) *Attorney, Agent, or Firm*—Fitch, Even, Tabin & Flannery

(57) ABSTRACT

A portable, self-contained, electronic radioscopic imaging system uses a pulsed X-ray source, a remote X-ray sensor, and a self-contained, display and controller unit to produce, store, and/or display digital radioscopic images of an object under investigation in low voltage imaging environments such as medical applications including mammography and tissue imaging, and industrial radiography of low-density structures, or the like. The radiographic system uses an X-ray converter screen for converting impinging X-ray radiation to visible light, and thus each point impinged on the screen by X-ray radiation scintillates visible light emissions diverging from the screen. An image sensor, i.e., a CCD camera, is configured to sense the visible light from the screen. An aspheric objective lens operable with the CCD camera spatially senses visible light within a collection cone directed outwardly from the image sensor. An emission modification lens layer, e.g., a prismatic brightness enhancement film, through which the visible light emitted from the screen is transmitted is superposed with the screen and positioned in an optical path between the aspheric lens and the screen for generally focusing the diverging visible light as a restricted cone of illumination propagating outwardly from each point impinged on the screen to increase the fraction of light directed into the collection cone of the first lens and reducing the amount of scattered visible light from the screen.

26 Claims, 11 Drawing Sheets

U.S. PATENT DOCUMENTS

| | | | | |
|---|---|---|---|---|
| 5,412,705 | * | 5/1995 | Snoeren et al. | 378/98.3 |
| 5,434,418 | | 7/1995 | Schick | 378/98.8 |
| 5,452,337 | | 9/1995 | Endo et al. | 378/4 |
| 5,454,022 | | 9/1995 | Lee et al. | 378/98.8 |
| 5,550,380 | | 8/1996 | Sugawara et al. | 378/98.3 X |
| 5,584,292 | | 12/1996 | Cheung | 378/98.3 X |
| 5,608,774 | | 3/1997 | Polichar et al. | 378/98.8 |
| 5,617,463 | * | 4/1997 | Beierlein | 378/98.3 |
| 5,724,402 | * | 3/1998 | Grady | 378/98.3 |
| 5,828,726 | | 10/1998 | Polichar et al. | 378/98.2 |
| 5,909,478 | | 6/1999 | Polichar et al. | 378/98.2 |

OTHER PUBLICATIONS

Tannas, "Evolution of Flat–Panel Displays", *Proceedings of the IEEE,* 82:4, pp. 499–509 (Apr. 1994).

Antonuk, et al., "Considerations for High Frame Rate Operation of Two–Dimensional a–Si:H Imaging Arrays", *Materials Research Society Symposium Proceedings,* 297:945–950 (1993).

VIDISCO, Ltd., Sales Brochure for "A–500E Portable Video Based X–Ray Inspection System" (1994).

* cited by examiner

ENHANCED X-RAY CONVERTER SCREEN FOR X-RAY RADIOSCOPIC SYSTEMS

CROSS-REFERENCE TO RELATED APPLICATIONS

This application is a continuation-part of application Ser. No. 09/076,604, filed May 11, 1998 now U.S. Pat. No. 5,909,478, which is a divisional application of Ser. No. 08/773,483, filed Dec. 23, 1996, now U.S. Pat. No. 5,828,726, which is a continuation of application Ser. No. 08/494,251, filed Jun. 23, 1995, now U.S. Pat. No. 5,608,774.

BACKGROUND OF THE INVENTION

The present invention relates to a portable, self-contained, X-ray apparatus that digitally processes, displays, stores, and/or transmits electronic radioscopic images of sealed packages, containers, or other objects, or of patients and animals, on location for security, customs, medical, and other non-destructive and non-invasive purposes. More particularly, the present invention relates to an enhanced X-ray converter screen for use in X-ray radioscopic imaging systems which increases the detected brightness and reduces the effects of veiling glare and multiple reflections through the use of thin film lenslets or other light directing films or structures which simultaneously modify the emission angle of light from the screen and change its reflective characteristics to external light through the use of thin film lenslets or other light directing films or structures which simultaneously modify the emission angle of light from the screen and change its reflective characteristics to external light.

There are many instances in the medical, security or customs field when it is necessary to examine or inspect, in a non-invasive way, a patient, animal, or other living organism; or to examine and inspect, in a non-destructive way, the contents of a closed package, box, suitcase, or other container. Some of the general concerns and problems associated with such examinations or inspections are set forth in U.S. Pat. No. 5,608,774, incorporated herein by reference.

Where the imaging system uses an objective lens coupled through a collection cone to a phosphor X-ray conversion screen, as is common in many radioscopic imaging systems, there is a continuing need to improve the brightness and contrast of the displayed image. This is because such systems are premised on the assumption that all of the emitted light from the phosphor screen is collected into the collection cone of the objective lens, thereby providing a clear, sharp image of the emitted light. In practice, however, some of the emitted light is not collected into the collection cone and is scattered by objects within the imager enclosure back onto a different portion of the phosphor screen, from which location it is then diffusely reflected, with a fraction of the light being sent back into the collection cone. Since this light appears to originate from a differing point on the phosphor screen, it effectively reduces the true contrast of the image.

Virtually all optical designs are plagued by the problem of light outside of the capture cone of the lens hitting other features within the optical system and being scattered back into the image. Generally, prior art designs attempt to solve this problem by making the walls of the system physically distant from the beam, using a series of anti-scatter baffles just outside of the optical path, and coating all surfaces with a very non reflective material. The literature contains designs for such systems as well as the formulations of paints and surface treatments for accomplishing these goals.

Unfortunately, the above approaches are very difficult to use in a mirror folded system, such as is used for many X-ray imaging systems, including the present invention. Further, if one wants to restrict the depth of the optical system (which is the case with the present invention) by using a mirror angle of 45 degrees or less, the problems of containing the light emitted at angles that would normally not fall into the collection cone and keeping this light from reflecting back onto the diffuse phosphor surface (where it may then bounce back into the collected beam) becomes virtually impossible.

It is thus evident that improvements are needed within X-ray radioscopic imaging systems, as well as any imaging system that uses light emitted from a diffuse phosphor screen into the collection cone of an objective lens, that both: (1) increase the fraction of light from the phosphor converter screen that is collected into the collection cone of the objective lens, and (2) which reduce the effects of light emitted from the diffuse phosphor screen not captured by the lens.

The present invention addresses the above and other needs.

SUMMARY OF THE INVENTION

The present invention enhances the optical portion, or "imager", of an X-ray radiographic or similar optical imaging system by increasing the fraction of light emitted from an X-ray converter screen that is directed into the collection cone of an objective lens, while at the same time reducing the effects of light emitted from the X-ray converter screen (which comprises a diffuse phosphor screen) which leaves the screen in a direction that is not captured by the lens. That is, the invention reduces the amount of light that is permitted to scatter within the imager, and also suppresses any light that does scatter within the imager. By reducing the amount of scattered light, and by suppressing what light does scatter, the collection cone of the objective lens thus receives a greater portion of the emitted light, and the optical system is thus able to produce a brighter image having improved contrast than has heretofore been achievable.

In accordance with one aspect of the invention, the amount of light permitted to scatter within the imager is reduced by focusing more light toward the center of the collecting lens through the use of thin light directing films or structures.

In accordance with another aspect of the invention, the effects of re-scattered light within the imager are suppressed, or minimized.

In general, one of three basic ways may be used to both intensify on-axis light (focused light) captured by the lens and to reduce or suppress off-axis light (scattered light). First, a baffle-like structure or film that functions much like a venetian blind (sometimes referred to herein as a "Chevron structure") may be used to limit the angle of emission (and transmitted intensity) of the light that is directed to the lens. Second, the light directed to the imaging lens may be refocused with a sheet of tiny microlenses or one or more linear micro prism structures adapted to collect a large fraction of the light emitted below their collection surface area. Advantageously, such refocusing elements have a focal point very near the imaging screen's surface (thereby allowing the light to be highly focused); or, by proper choice of orientation, such refocusing elements may actually redirect an already restricted emission to incline its center more into the collection cone and away from any other surfaces within the enclosure. Further, for that light which does scatter back from the walls of the enclosure, it may be made to strike specific reflecting surfaces rather than the diffuse surface of the screen so that the likelihood of the light being scattered into the collection cone is reduced. Third, combinations of the first and second re-scattering reduction techniques described above may be used in a correlative manner so that their combined effects add in a beneficial way to both reduce off axis light as well as intensify the on-axis light captured by the lens.

In accordance with another aspect of the invention, appropriate linear structures may be used along a single axis, providing enhanced optical properties in one dimension, or crossed linear structures may be used along two axes, providing enhanced optical properties in two dimensions.

The invention is particularly applicable in situations where the light from the conversion screen is limited. Such situations occur in low voltage, X-ray imaging systems where the light emitted per X-ray photon is weak due to the intrinsic low energy contained in the individual X-rays. Primary applications of this type include, among others, medical applications, e.g., mammography and tissue imaging. Alternatively, one also finds the same situation in industrial radiography of low-density structures such as composite materials. At the other extreme are cases in which the X-ray conversion screen (which converts X-ray energy to light), has been chosen to be of a very high density to provide good interaction efficiency but where the phosphor does not convert the energy to light with great efficiency. In either case, one of the aspects of the present invention is directed to-improving the amount of light captured from the screen into an optical system and subsequent imager. The light collection may be a function of (1) the initial X-ray energy flux, (2) the probability of interaction within the screen, (3) the energy to light efficiency, or (4) the optical collection efficiency of the lens or other optical system. The described embodiment is directed particularly to improving light collection by way of the last term in the equation, i.e., the optical collection efficiency.

Since the goal of a good imaging system is to bring down all sources of noise to a level below one X-ray photon, it is important that each X-ray event produce the highest detectable light output possible. This is the primary of effect of the enhanced X-ray converter screen for radioscopic systems described herein. The additional benefit is that the internal scattering of light within the imager enclosure is significantly reduced which also benefits the image quality by extending the range of penetration into the darker portions of the image.

It is thus an object of the invention to employ light-directing films or Chevron-like structures within the optical portion of an X-ray radiographic or similar optical imaging system that provide simple masking of emission angles so as to better direct the reflected light into the collection cone.

It is another object of the invention to provide light-directing structures within the optical portion of an X-ray radiographic or similar optical imaging system that use the refractive power of an array of lenslets or linear microprisms.

It is yet another object of the invention to provide an X-ray converter screen and a method of converting X-ray radiation to visible light.

It is a further object of the present invention to provide a radiographic system employing an objective lens in which a visible light emission modification layer is superposed with an X-ray converter screen for generally focusing the diverging visible light as a restricted cone of illumination propagating outwardly from each point impinged on the screen to increase the fraction of light directed into the collection cone of the objective lens while reducing the amount of scattered visible light from the screen.

An advantage provided by the invention is that such light-directing films or structures effectively concentrate the emission angle of the normal lambertian pattern and redirect the centroid of that angular distribution toward the center of the collecting lens, thereby providing an enhanced image for the imaging system. In effect, this approach trades off an increase in brightness and reduction in off axis emission for the spatial quantification of the totality of light emitted from under each lenslet, microprism or other structure.

In a described embodiment, a radiographic system uses an X-ray converter screen for converting impinging X-ray radiation to visible light, and thus each point impinged on the screen by X-ray radiation scintillates visible light emissions diverging from the screen. An CCD camera image sensor is configured to sense the visible light from the screen. An aspheric objective lens operable with the CCD camera spatially senses visible light within a collection cone directed outwardly from the image sensor. An emission modification lens layer may be provided as a prismatic brightness enhancement film, through which the visible light emitted from the screen is is transmitted is superposed with the screen and positioned in an optical path between the aspheric lens and the screen.

Briefly summarized, the present invention relates to a radiographic system and an X-ray converter screen including a substrate for converting impinging X-ray radiation to visible light, each point impinged on the substrate by X-ray radiation scintillating visible light emissions diverging from the substrate. An emission modification layer through which the visible light emitted from the substrate is transmitted generally limiting the diverging visible light to a restricted cone of illumination propagating outwardly from each point impinged on the substrate by the X-ray radiation. The invention further relates to a method of converting X-ray radiation to visible light by providing an X-ray converting screen, and then superposing the screen with a transmissive film for modifying the transmission of visible light emitted from the screen to generally limit the diverging visible light to a restricted cone of illumination propagating outwardly from each point impinged on the screen by the X-ray radiation.

From an imaging system point of view, and with particular reference to the disclosure provided in the '774 patent, a goal of the present invention is to use the enhanced optical system herein described within a completely digital imaging system capable of recording and digitizing the individual X-ray image data, including the ability to store and retrieve that data onto a suitable storage medium, such as a hard disk of a portable computer. Such portable computer may then serve as a controller for selectively displaying the image in a way that reveals the full dynamic range and resolution of the sensor. In addition, the image captured by the system may be transmitted to remote locations (when necessary) via a modem for evaluation by experts who are not on site.

The above and other goals are met by providing a portable, self-contained, electronic radioscopic imaging system. Such system typically includes three main subsystems: (1) an X-ray source, (2) a remote X-ray sensor, or "imager", and (3) a self-contained, display and controller unit, or "display/control unit." The X-ray source emits X-rays at the object being investigated. The X-ray sensor or imager utilizes a scintillating screen that produces flashes of light when impinged by an X-ray in combination with either an integrating CCD camera, or an active matrix of thin film transistors and thin film sample-and-hold photodiodes, to produce an integrated signal that represents the sum of the radiation that pass through the object in a given pixel area.

Advantageously, the light directing films or structures described herein, when used within the imager, produce an image exhibiting more brightness and better contrast than has heretofore been available in an imaging system of this kind. The self-contained display and control unit utilizes digital signal processing within an enhanced portable computer, including a solid-state flat panel display and associated drive circuitry, in order to display to an operator the full dynamic range and resolution of an image-capturing sensor utilized within the imager. A modem further permits the digitized image to be sent to a remote location where the exact same image can be recreated for analysis by off-site experts.

Other features of the imaging system may be the same as, or substantially similar to, those described in the '774 Polichar et al. patent, previously incorporated herein by reference.

BRIEF DESCRIPTION OF THE DRAWINGS

The above and other aspects, features and advantages of the present invention will be more apparent from the following more particular description thereof, presented in conjunction with the following drawings wherein:

FIG. 5 is a perspective view of a special shield that is used to shield the CCD camera included in FIG. 3A;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
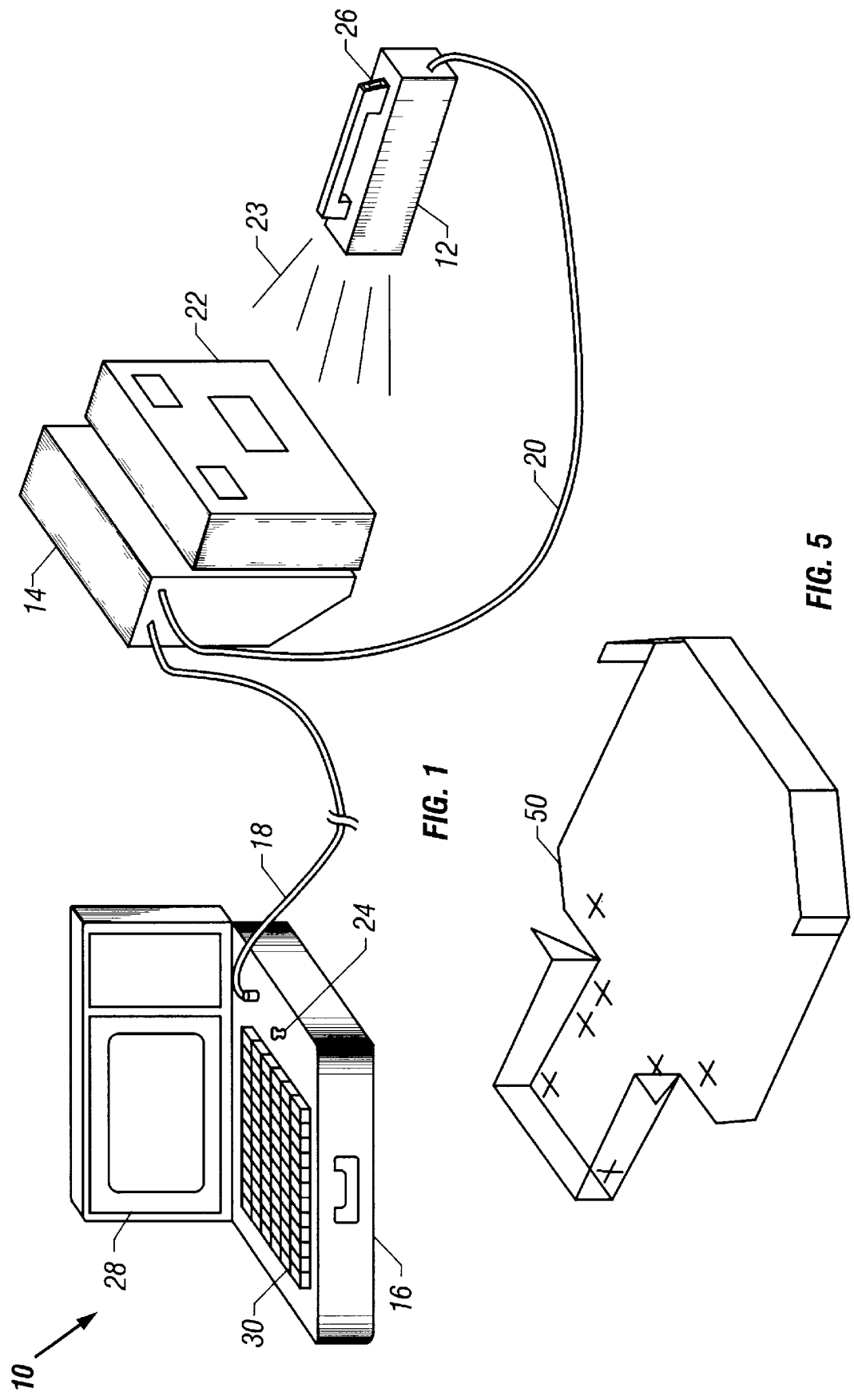
FIG. 1 depicts an imaging system in accordance with the present invention as it is used to form a radiographic image of a package under investigation.

Turning first to FIG. 1, there is shown an imaging system 10 made in accordance with the present invention. The system 10 includes three main subsystems: (1) a portable X-ray source 12, (2) an imager 14, and (3) a Display/Control Unit 16. The three subsystems are interconnected with two cables. A first cable 18 is a "long" cable and is connected between the Display/Control unit 16 and the imager 14. The long cable may be as long as 180 feet. A second cable 20 is a "short" cable that is connected between the imager 14 and the X-ray source 12. The short cable is typically less than 10 feet in length.

Advantageously, the system 10 is portable, which means it is sufficiently lightweight and non-bulky to enable a single person to hand-carry its three constituent subsystems and associated cables to a field location where an object 22 to be investigated is located. Once on site, the system 10 is designed to: (1) facilitate quick and easy setup around the object 22 to be investigated, (2) provide rapid image acquisition at the field location, and (3) provide image enhancement tools that aid in the evaluation of the acquired image.

In operation, the system 10 is setup by placing imager 14 next to the object 22 to be investigated, e.g., as close as possible to the object. The X-ray source 12 is then placed, e.g., two to three feet from the imager 14, on the opposite side of the object 22. The display/control unit 16 is then connected to the imager by way of the long cable 18 and is placed a safe distance from the object 22. The X-ray source is also connected to the imager 14 by way of the short cable 20. When everything is properly connected, all three subsystems are turned on, and under control of the display/control unit 16, the X-ray source 12 generates a pulsed X-ray beam (represented by the lines 23) that is allowed to pass through the object 22. The pulsed X-rays pass through respective segments of the object 22 with varying degrees of intensity, or energy, as a function of the contents of the object 22, and are captured or sensed at corresponding pixel areas of the imager 14. The intensity or energy of these pulses that pass through the object 22 are accumulated or summed (integrated) over the duration of the pulsed beam (exposure time), which exposure time may include, e.g.,. a burst of 15–99 pulses.

At the conclusion or termination of the pulsed beam, the imager 14 has acquired an integrated or summed energy for each pixel of the display area, with the combined collection of all such energies for all the pixels comprising an integrated image signal. The integrated image signal is then transferred to the display/control unit where it is appropriately processed and displayed. Such processing includes digitizing the signal to facilitate its subsequent storage, retrieval, enhancement, display and/or transmission.

Advantageously, the system 10 is designed for safety and ease of operation. X-ray safety is assured, e.g., through the use of the pulsed X-ray source 12. Such pulsed source produces extremely short bursts of X-rays capable of penetrating several inches of most materials, yet generates extremely low radiation dose (integrated exposure) levels outside the direct source beam. Safety is further enhanced by two interlock keys, both of which must be in place and in the "ON" position in order for the X-ray source 12 to be activated. A first interlock key 24 is at the display/control unit 16. A second interlock key 26 is at the X-ray source 12. Moreover, a software interlock is provided as part of the operation of the display/control unit 16. Such software interlock generates and displays a warning message on a screen 28 on the display/control unit 16 and then requires the operator to acknowledge such warning message by pressing a key on a keyboard 30 of the display/control unit 16 before the X-ray source can be triggered.

An additional safety feature is provided through the use of the long cable 18 which permits the display/control unit 16 (and hence the operator) to be located a safe distance (the length of the cable 18) from the object 22 being investigated. The cable 18, for example, may be as long as 180 feet, although in the preferred embodiment it is only about 60 feet (typically provided through two 30-foot sections). The cable 18 could be made even longer, if desired, if appropriate line drivers are inserted into the line at regular intervals, and/or if a different transmission medium is used (e.g., fiber optic cable, and or RF wireless transmission).

Figure 2:
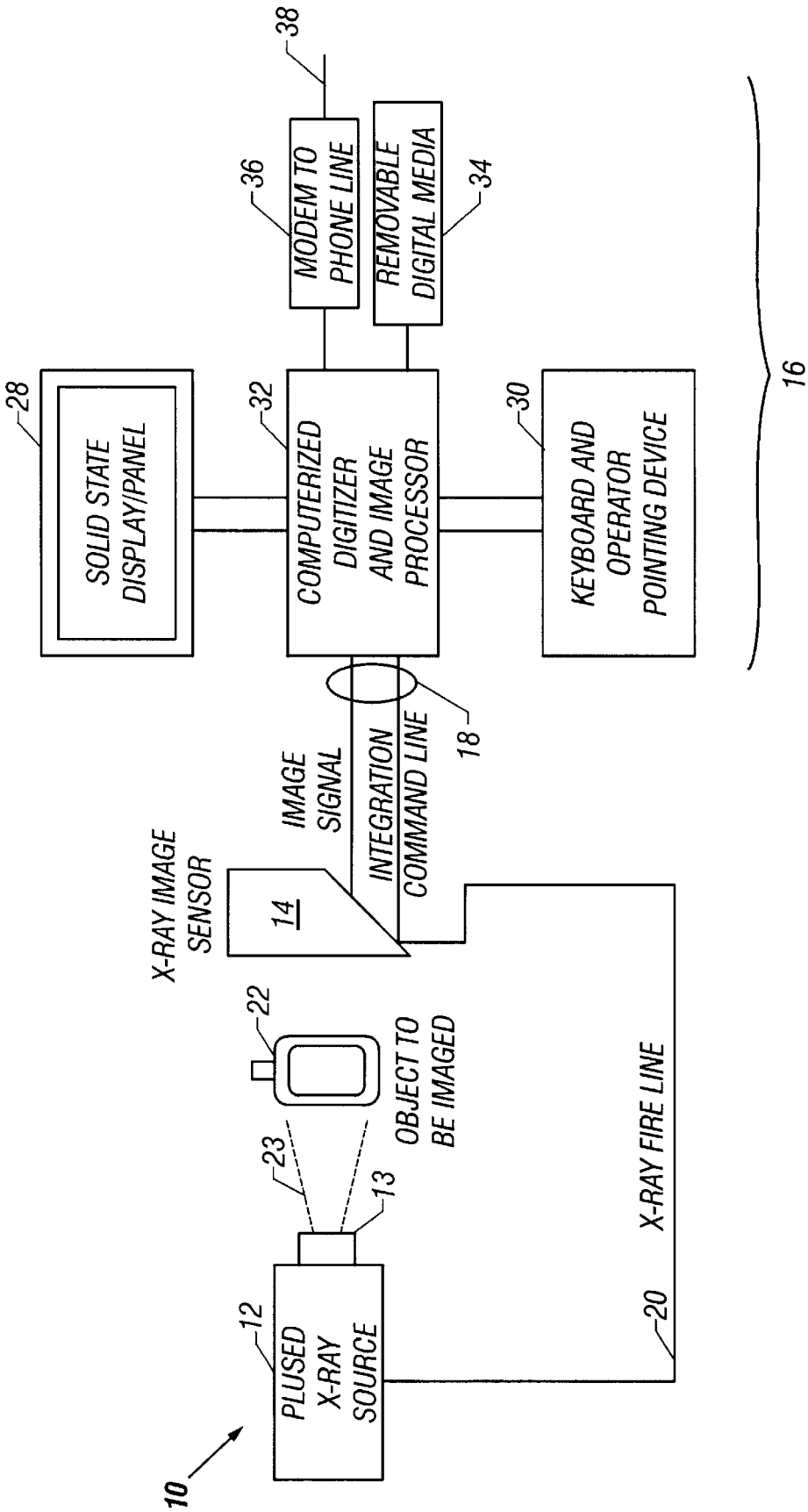
FIG. 2 is a block diagram of the imaging system.

Turning next to FIG. 2, there is shown another diagram of the imaging system 10 which illustrates, in block diagram form, essentially the same elements as are depicted in FIG. 1. However, FIG. 2 shows further detail of the display/control unit 16 (which hereafter may be referred to as simply the "control unit 16"), and in particular shows that the control unit 16 includes a computerized digitizer and image processor 32, a solid state display panel 28, a keyboard and operator pointing device 30, removable digital media 34, and a modem 36 to allow connection to a phone line 38. The long cable 18 connects between the computerized digitizer and image processor 32 and the imager 14 (sometimes referred to herein as an "X-ray sensor"). The signals sent and received over the long cable 18 include the integrated image signal and a trigger signal, as well as an operating voltage (power) for the imager 14. The trigger signal triggers both the integration circuitry within the imager 14 as well as the X-ray fire line going to the pulsed X-ray source via the short cable 20.

Advantageously, the pulsed X-ray source 12 may be realized using any suitable commercially available X-ray source. One commercially available X-ray source that may be used within the system 10, for example, is the Golden Inspector® Model 200 X-ray source manufactured by Golden Engineering Inc., P.O. Box 175, Centerville, Ind., 47330, the operator's manual for which is incorporated herein by reference. The Inspector Model 200 X-ray source has a maximum output energy of 150 kV, and produces about 3.0 mRem output dose per pulse at one foot (on the beam centerline, with 2.5 mm aluminum filter). It includes a built-in electronic counter to provide from 0–99 pulses. The X-ray pulses are generated have a nominal pulse width of 50 nanoseconds. The nominal pulse rate is 20–25 pulses per second (pps). It is a modular design having approximate dimensions of 4.2 inches wide by 4.2 inches deep by 15 inches long. It weighs only 20.5 pounds with a battery. It also includes a standard camera tripod mounting plate (20¼ thread). Besides a battery, it includes a power cord and self-contained 29 volt rechargeable battery pack. The source 12 may be battery operated or it may be plugged into a 110/220 VAC, 50/60 Hz power outlet using conventional power cords. Switching between battery and line power is automatic. Other equivalent portable X-ray sources could, of course, be used in lieu of the Golden Inspector Model 200 X-ray source.

The X-ray source 12 should be positioned so that the beam centerline intercepts the "imager screen" near its center. The imager screen is that portion of the imager 14 designed to be impinged by the pulsed X-rays that pass through the object 22, and hence that portion of the imager which captures the X-ray image. One of the advantages of using the modular X-ray source 12 is that it can be readily adjusted in height and orientation by positioning it on the floor, on risers, or on an adjustable platform, as required. The imager 14 may also be adjusted, as required, so that the region of interest of the object 22 is as close as possible to the imager screen. The location of the imager screen on the imager 14 may be denoted by a rectangular indentation on the face of the imager 14, or by other suitable markings (e.g., painted lines). The X-ray source is preferably positioned approximately two to three feet from the imager screen for best image results.

It is also preferred that a suitable X-ray source beam filter 13 (FIG. 2) be used with the X-ray source 12 in order to enhance the quality (resolution and contrast) of the resulting image. An X-ray filter typically comprises a thin metal sheet that is placed over the exit aperture of the X-ray source to remove by absorption and scatter a fraction of the low energy X-rays. It has been found that, depending on the thickness and material composition of the object imaged, very low energy X-rays in the source beam may not be contributing to the formation of the X-ray image formed (which X-ray image is, in essence, an X-ray "shadow" of the object(s) placed in the path of the X-ray beam) by transmission through the object. These low energy X-rays, however, are believed, in some instances, to decrease the quality of the image by contributing to statistical noise, thereby resulting in a decrease in image resolution and contrast through scattering. Hence, the filter 13 is used to remove such low energy X-rays. The type and thickness of the filter 13 to be used typically depends on the thickness and composition of the object.

When imaging a thin, or lightweight target, the filter 13 should be of minimal thickness, such as 0.005 to 0.010 inch thick copper or 0.020 to 0.030 inch thick aluminum. If the target 22 contains dense materials, a more substantial filter 13 may give better results. A copper filter of 0.020 inch thickness may help image effectively steel objects. Alternatively, use of a 0.050 inch thick aluminum filter is also believed to produce satisfactory results.

The problem of imager saturation, sometimes referred to as "blooming", can be corrected by decreasing the exposure time. It has also been learned that imager saturation can be lessened using a suitable beam filter 13. When trying to image objects which have adjacent areas of high and low density materials, saturation of the less dense regions can hide detail in the dense areas. By employing the different thicknesses of filtering materials, it has been found possible to reduce or even eliminate this "blooming" problem, reduce noise due to scattering, and produce a more detailed radioscopic image.

Figure 3A:
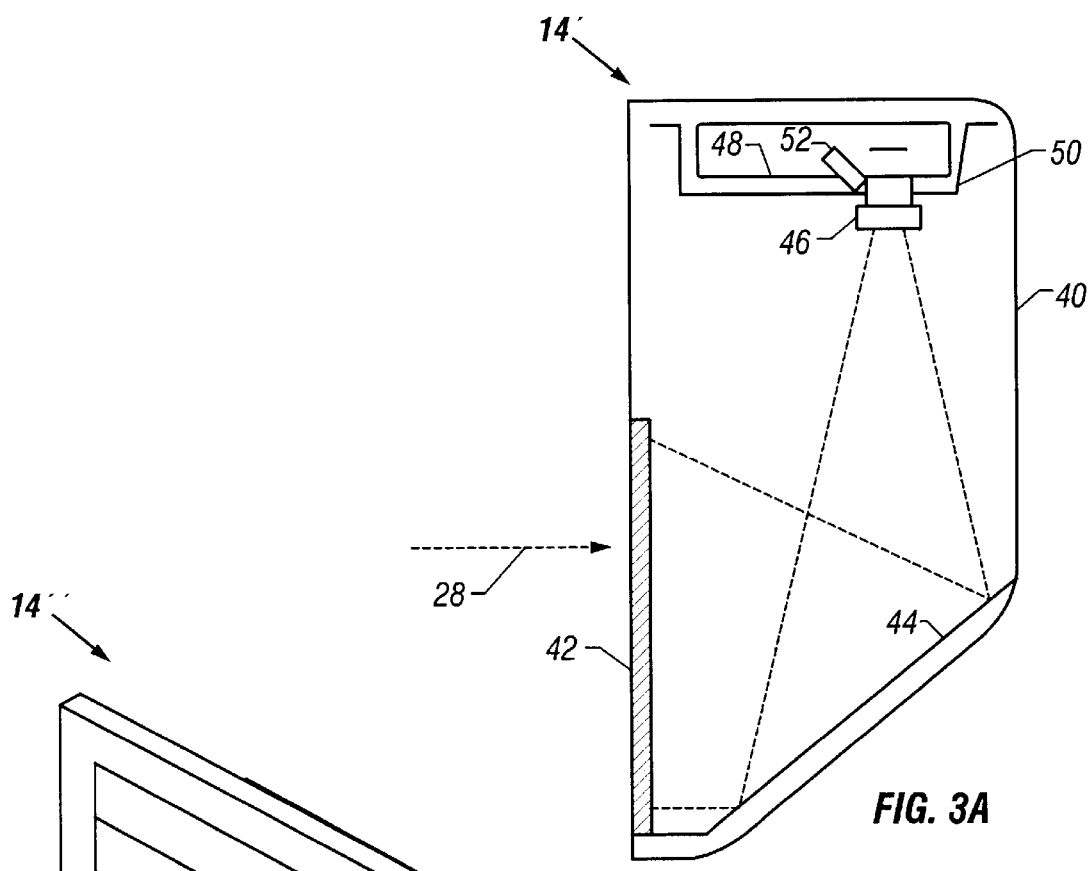
FIG. 3A illustrates a CCD camera version of the X-ray sensor used with some embodiments of the system of FIGS. 1 and 2.

The imager 14 is realized by application of a suitable X-ray sensor. One type of X-ray sensor that may be used for the imager 14, for example, is an integrating CCD camera subsystem 14' modified in accordance with the present invention, as shown in FIG. 3A. As seen in FIG. 3A, the CCD subsystem 14' includes a lightweight metal housing 40, e.g., made from 0.06 inch thick aluminum, that holds an X-ray light converter screen 42, which screen 42 functions as the "imager screen" referred to above. Typically, the screen 42 is eight by ten inches in size, and is realized using a suitable scintillating screen, e.g., a phosphor scintillating screen. As the X-rays strike a particular pixel area of the scintillating screen 42, flashes of fluorescence occur having an intensity or energy proportional to the energy of the X-ray beam. Such flashes are then optically guided through a suitable optical path, which includes a front surface mirror 44, through a fast lens 46, to a solid-state, compact, integrating charge-coupled device (CCD) camera 48.

The image is recorded within the CCD camera 48, and is converted to a standard video signal that is sent to the control unit 16 via the long cable 18 (FIGS. 1 and 2). The housing 40, in the preferred embodiment of the imager 14', includes a built-in handle to help transport it. Such handle may also be positioned to help hold or support the housing so that the screen may be maintained in a generally vertical position when the imager 14' is oriented as shown in FIG. 3A.

A preferred imager 14' has approximate dimensions of 10.3 inches wide by 12 inches high and 7 inches deep. The weight of the imager 14' is under 10 pounds, operating power for the imager 14' is obtained through the cable 18 from the control unit 16, and is typically provided by way of a power supply voltage of 12 volts. Hence, like the other components of the overall system 10, the imager 14' is readily portable and easy to use at an on-site field location.

As indicated previously, the CCD camera 48 integrates the image over a prescribed number of X-ray pulses (exposure time). Advantageously, the integration of the light image (resulting from the flashes of fluorescence that occur as the X-ray pulses impinge the scintillating screen) occurs on the CCD chip, as opposed to being carried out using off-chip electronic circuitry. The normal charge readout is inhibited during the integration period, thereby making such charge readout available at the completion of the integration period for use as the standard video signal, or integrated signal, previously referenced. Further, integration only occurs in synchrony with the generation of the burst of X-ray pulses, thereby effectively blocking out "noise" that is present at times other than when the X-ray burst is present.

In the preferred embodiment of the imager 14', the CCD camera 48 is realized using an 1100 Series Board Level Monochrome CCD Camera obtained from Cohu, Inc. 5755 Kearny Villa Rd., San Diego, Calif., 92123. The 1100 Series CCD cameras feature a ½ inch-format on-chip microlens sensor, mounted to an electronic board whereon supporting electronic circuitry is placed, such as driver circuits, video generation circuits, power supplies, and the like. Advantageously, the 1100 Series cameras may readily be configured for custom purposes. In this instance, the only significant modification that needs to be made to the 1100 Series CCD Camera obtained from Cohu is to change the integration time of the camera from being controlled by a start/stop pulse, to being controlled by an exposure time (number of pulses) so that integration occurs only during the pulsed X-ray burst, and not at other times. Even this modification would not be required is one chose to generate a separate start/stop pulse coincident with the beginning and ending of the exposure time. However, by making the modification indicated above, the need for such a separate start/stop pulse is eliminated, thereby reducing the number of signals that need to be communicated through the long cable 18.

With a Series 1100 CCD camera (or equivalent camera where a microlens sensor is mounted on an electronic board), it has been found that the CCD camera 48 needs to be protected from exposure to ionizing radiation damage. Two types of problems may arise. First, X-rays which penetrate the imager 14' without interacting with the scintillating screen 42 may strike the CCD chip of the camera 48. If this happens, visible specks of white light appear on the image, thus reducing the image quality. Second, prolonged exposure to such radiation can prove to be harmful to the integrated circuit components, e.g., the CCD chip or other integrated circuits used to generate the video signal, possibly resulting in failure of such circuits.

In order to reduce the number of X-rays that strike the camera 48, the camera 48 is encased in a 0.125 inch thick lead housing or shield 50. The preferred shield 50, for use with the particular CCD camera 48 specified above, is shown in its folded state in FIG. 5, before placing it around the CCD camera 48. In addition, a 0.25 inch thick lead plate 52 may be placed between the CCD-chip and incident X-ray radiation in order to further shield the CCD chip from stray X-rays.

A further aspect of the invention concerns the use of the first surface of the mirror 44 (FIG. 3A) to direct the image of the scintillating screen 42 to the CCD camera 48. Employing the mirror 44 as shown, i.e., in line with the X-rays that strike the scintillating screen, permits placement of the CCD camera 48 at a location outside of the main X-ray path, thereby significantly reducing the number of X-rays that might otherwise directly strike the CCD camera or its associated electronic components. (Note, any the X-rays that pass through the scintillating screen 42 would also pass through the mirror 44.)

As indicated, the preferred CCD camera 48 is an 1100 Series CCD camera made by Cohu of San Diego, Calif. Representative specifications of the Cohu's 1100 Series camera are as follows:

| | |
|---|---|
| Pick Up Device: | ½" Interline transfer, microlens sensor |
| Active Picture Elements: | RS-170: 768 (H) × 494 (V) |
| | CCIR: 752 (H) × 582 (V) |
| Pixel Cell Size: | 8.4 µm (H) × 9.8 µm (V) |
| Total Pixel Elements: | 811 (H) × 508 (V) |
| Resolution: | RS-170: 580 horizontal TVL, ≧350 vertical TVL |
| Synchronization | Horizontal and Vertical Crystal (RS-170) Asynchronous reset |
| Shutter | 1/60 to 1/10000 |
| Power | 12 VDC, 3.6 W max |
| Size | 1.75 × 3.88 × 1.00 inches |

Figure 3B:
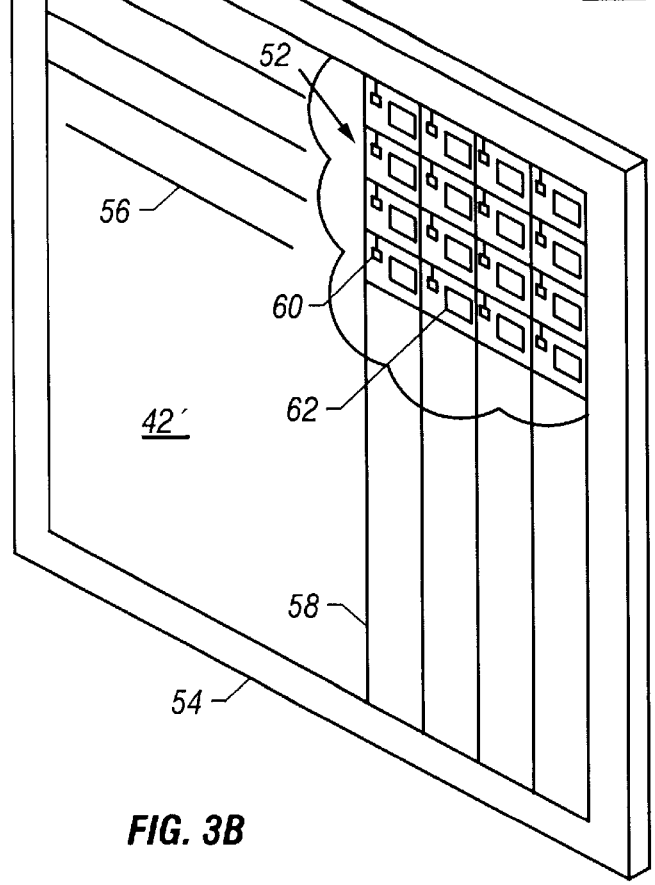
FIG. 3B depicts a TFT flat panel amorphous silicon X-ray sensor used with other embodiments of the system of FIGS. 1 and 2.

Another type of X-ray sensor that may be used as the imager 14 is a flat panel sensor 14", as shown in FIG. 3B. Such sensor 14" offers the advantage of being flat and relatively thin so that it can be positioned into tight spots, and further eliminates the need for a mirror(s) and/or lenses to define an optical path. The sensor 14" includes a conventional X-ray scintillation screen 42' that is in direct contact with a flat panel, amorphous silicon, TFT (thin film transistor) photo sensor 52. The TFT photo sensor 52 is made on a glass or ceramic substrate 54, and includes a matrix of thin film transistors 60. Each TFT further has its own thin film sample and hold (S&H) photodiode 62 associated therewith. The matrix of TFT's and S&H diodes is sufficiently dense so that each TFT 60 and associated S&H photodiode 62 corresponds to a different pixel of the sensor 14". The S&H photodiode 62 senses and accumulates all of the light flashes produced at the corresponding pixel of the scintillation screen 42' during the integration time. At the end of the integration time, the accumulated signal at each pixel site that is held by the corresponding S&H photodiode 62 is read through its corresponding TFT transistor 60 through appropriate row drive electronics 56 and column drive electronics 58, in conventional manner. Such accumulated signals, for all of the pixels of the sensor 14", thus comprise the integrated image signal for a given exposure time.

Further details of the manner of making and using a flat panel sensor of the type illustrated in FIG. 3B as the sensor 14" are described, e.g., in Street, et al., "Amorphous Silicon Arrays Develop a Medical Image," *IEEE Circuits and Devices,* pp. 38–42 (July 1993); and Wu et al., "Imaging With Page-Sized A-Si:H 2-Dimensional Sensor Arrays," *SPIE Proceedings,* Vol 2172 pp. 144–154. Both of these references are incorporated herein by reference.

Figure 4:
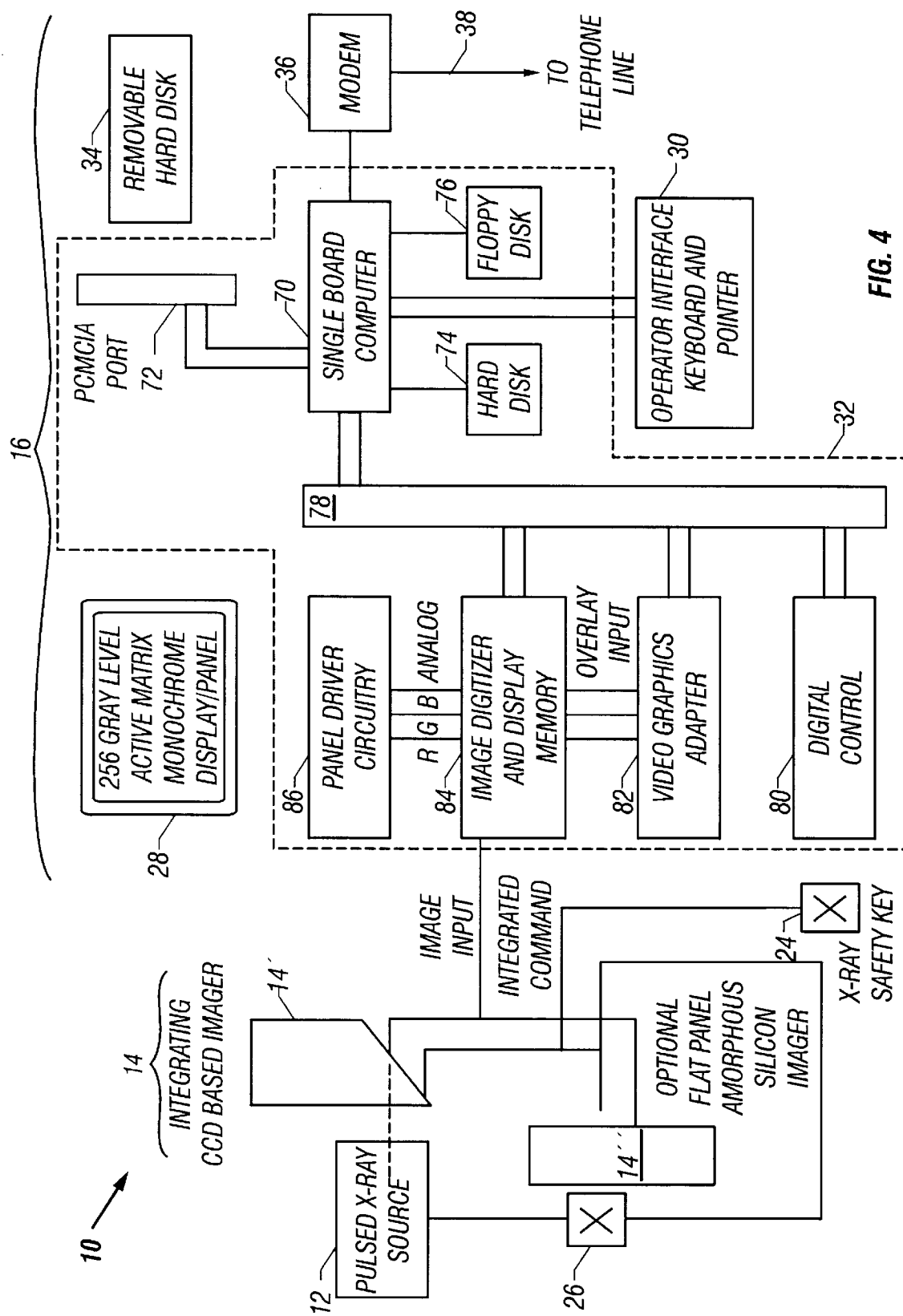
FIG. 4 is a block diagram of the imaging system and shows additional detail of the display/controller unit.

Turning next to FIG. 4, a more detailed block diagram of the imaging system 10, and particularly of the control unit 16, is illustrated. As seen in FIG. 4, at the heart of the control unit 16 is a single board computer (SBC) 70. The SBC 70 is connected in conventional manner to a PCMCIA port 72 (adapted to interface with a removable hard disk 34), a hard disk 74, a floppy disk drive 76, a keyboard/pointer 30, and a modem 36, all of which are of conventional design. The SBC 70 further interfaces, through a suitable bus 78, with digital control circuitry 80 (for generating-/interfacing the digital control signals that are sent to the imager 14 and the X-ray source 12), a video graphics adapter 82 and an image digitizer and display memory 84, all of which may also be of conventional design, except as indicated below. The image digitizer and display memory 84 further interfaces, through panel driver circuitry 86, with an active matrix monochrome display panel 28. Advantageously, all of the components of the control unit 16 are effectively those of a conventional personal computer (PC), with some modifications, as explained below.

While any suitable PC could be used and modified for use with the invention, the preferred PC is at a minimum a 486 class microprocessor, or better, operating at a preferred minimum clock speed of about 33 MHz, and modified as required to drive the active matrix monochrome display panel 28 so that it exhibits a large gray scale resolution, e.g., a gray scale that provides 256 different shades of gray. Such gray scale resolution is generally not commercially available, to applicant's knowledge, particularly in a small, transportable, ruggedized, self-contained, has-the-appearance-of-a-suitcase, unit. When modified, as explained below, the unit 16 has dimensions of only 18 by 13 by 7 inches, weighs only about 24 pounds (including a battery pack), and is housed in a "suitcase" housing that, when closed, does not readily identify its function. Such disguised appearance can be an important feature for some applications of the invention so that the unit can be easily carried into a desired field location, e.g., a busy airport terminal, without initially drawing undue attention thereto.

As indicated, most of the components of the control unit 16 are conventional components that may be provided by any suitable computer manufacturer. The principal exception to this general availability is the active matrix display 28 and associated driver 86. The use of a flat panel display 28 is very desirable for a portable system from a portability and ruggedness perspective. Advantageously, the use of a TFT flat panel display is particularly suited for the imaging system 10 because of the available brightness and wide range of available colors and grayscales. Disadvantageously, the use of TFT flat panel devices is complicated by the fact that they are relative recent additions to the display market, and the interface electronics to drive these displays, particularly for a monochrome application where a high grayscale resolution, e.g., 256, is desired, is not yet available. To further complicate matters, the signal to be displayed for the imaging system 10 is an analog VGA video signal, rather than a digital drive signal as is customarily used to drive such displays.

Figure 6A:
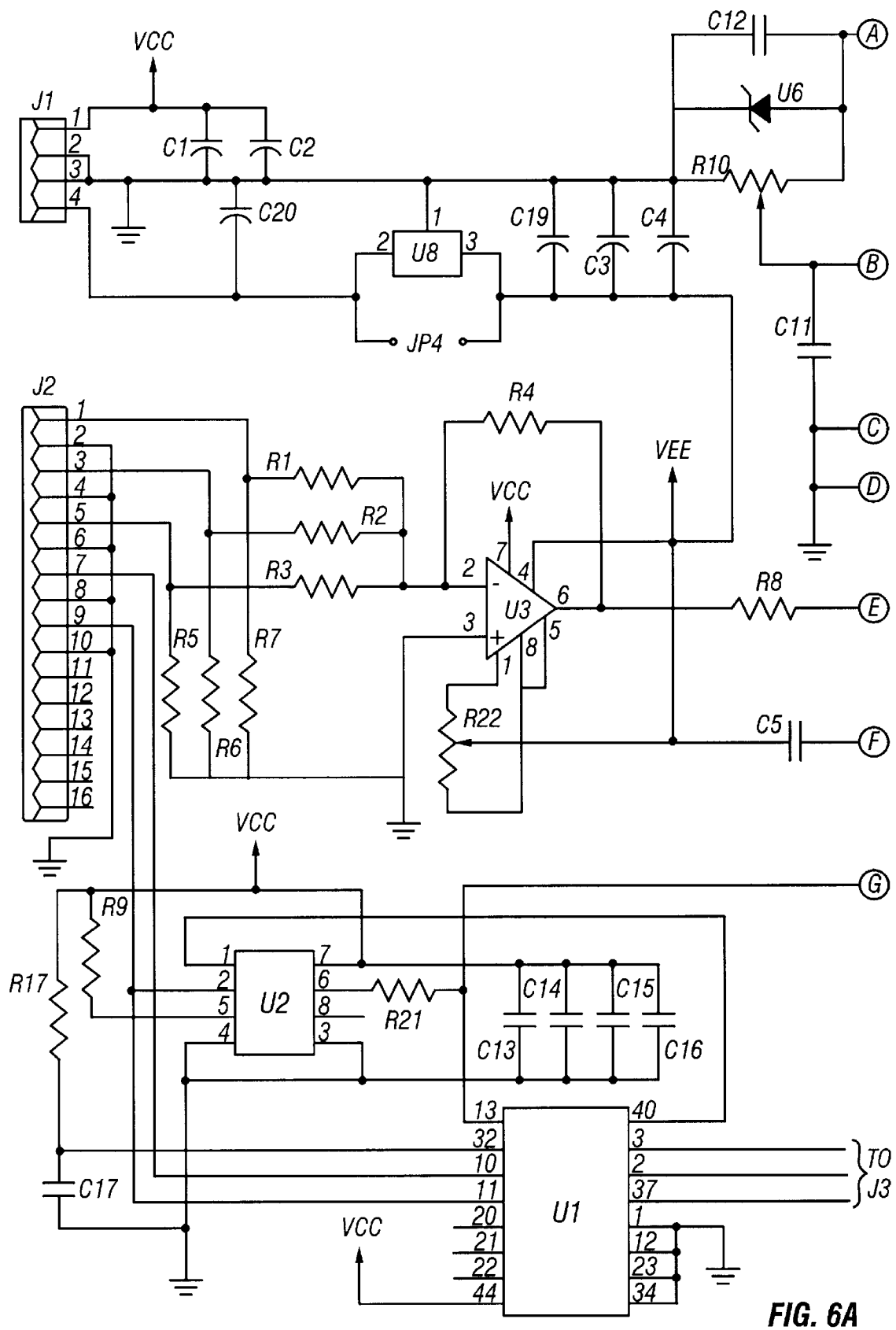
FIG. 6 is a schematic diagram of the panel driver circuitry of FIG. 4.
Figure 6B:
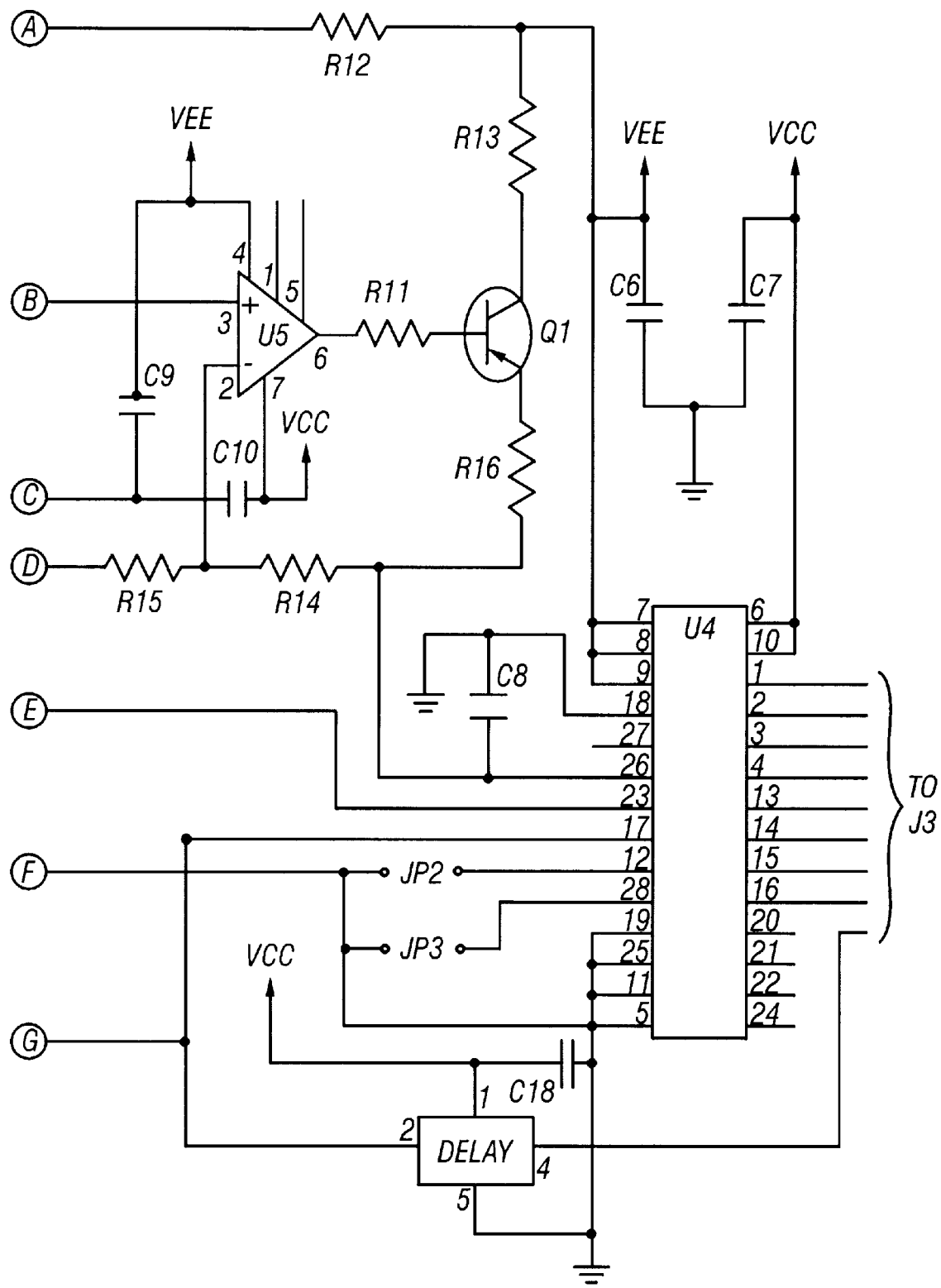

In view of the above difficulties, the present invention uses a custom panel driver circuit as shown in FIG. 6. The circuit in FIG. 6, explained more fully below, performs the function of converting the standard VGA signal, with its three component signals, red (R), green (G), and blue (B), to a digital signal suitable for driving the TFT active matrix flat panel display 28.

The preferred active matrix flat panel display for use with the control unit 16, but certainly not the only flat panel display that could be used, is a LDH096T-11 display made by Flat Panel Display Co. of Eindhoven, The Netherlands. The LDH096T-11 is a 9.5 inch diagonal LCD module that comprises an Active Matrix Liquid Crystal Display, an integrated adjustable backlight and module electronics. The module electronics facilitate interfacing with commercially-available VGA chipsets, and can display either 16 or 256 levels of gray depending on user selection. The display resolution of the LDH096T-11 is 640 by 480 dots, with a dot pitch of 300×300 $\mu$m. The contrast ratio is better than 60:1 at optimum viewing angles, and the brightness is 60 cd/m$^2$. The active area of the display is 192 by 144 mm. The power consumption, including backlight, is only about 2.5 Watts (nominal). The supply voltage for the display is 5 volts.

The panel driver circuit used to drive the LDH096T-11 display is shown in the schematic diagram of FIG. 6. The main signal inputs to the circuit shown in FIG. 6 comprise the RGB signals from the analog VGA signal, which signals are applied to connector J2 and directed to amplifier/summer U3, where they are multiplied by an appropriate gain factor and summed. The summing of the three RGB signals combines the signals, putting them on a single signal line (the output of amplifier U3). This summed/combined signal is then applied to analog-to-digital (A/D) converter U4, which converts the signal to an appropriate digital signal that can be applied to the display 28 through connector J3. The necessary clock signals and control signals needed by the A/D converter U4 and the flap panel display via connector J3 are generated in the programmable array logic contained in device U1. Other components, as well as control, timing and voltage signals, used within the circuit shown in FIG. 6 should be self-evident from the schematic diagram of FIG. 6 to those skilled in the electronic arts.

A preferred control unit 16 for use with the present invention comprises a modified SafeCase® Series 4000 Rugged Portable Computer made by Industrial Data Systems, Inc., 14900 Woodham Drive, Building 170, Houston, Tex. 77078-6016. The Series 4000 computer is ordered to include an 80486 microprocessor with a clock speed of 33 MHz, 8 MB of RAM, a 3.5" high density floppy disk drive, and at least a 210 MB hard drive. The basic unit offered by Industrial Data Systems (IDS) as specified above is further modified for 120/220 VAC 50/60 Hz/12 VDC operation, including a battery charger that charges the battery automatically whenever the unit is connected to a 120/220 VAC power line. To enhance battery operation, a Microbus MAT 752 low power 486DX/33 CPU board is installed in the unit 16 as the SBC 70. With such low power CPU board, a fully charged battery pack permits 75 to 80 minutes of operation of the unit. The charge level of a given battery pack can be tested at any time using a built-in push button and LED display located at the lower right corner of the battery pack. The battery packs may also be charged external to the unit 16 using a suitable battery pack charger.

As additional modifications to the Series 4000 Portable Computer, an Interlink Durapoint mouse pad pointing device, or other pointing apparatus, is built into the top panel the case (or otherwise made available to the user). Preferably, such pointing apparatus is positioned to be centered just below the keyboard so that a user can manipulate it with his/her thumbs while keeping his/her fingers on the keyboard. A PCMCIA Type III connector is also added to the top panel, and the Microbus CPU Board is connected to drive this port. It is through this port that removable storage media, or other peripherals, may be connected to the Microbus CPU Board. In addition, the I/O (input/output) expansion plate of the unit is punched to accept an Amphenol #165-159236 connector and cable, which when installed and connected to the Microbus CPU Board, functions as the connector for the long cable 18. The LCD panel is modified to accept the above-described FPD LDH096T-11 display 28, and the panel driver circuitry 86 (shown in FIG. 6) is appropriately installed within the unit 16 so as to drive the display 28 as controlled by the Microbus CPU board. Also installed in the unit 16 is an internal modem and external RJ-11 jack to facilitate modem communications.

The image digitizer and display memory 84 (sometimes referred to herein as simply the "image processor" 84) comprises a separate or auxiliary processor installed within the control unit 16 in order to facilitate the receipt, processing, and display of the integrated signal from the imager 14. Such image processor 84 may take several forms, and there are numerous commercially-available processor boards that could be used for this purpose. At the present time, one of two commercially available processors is preferred for use as the image processor 84, both of which are manufactured and sold by Matrox Electronic Systems, Ltd., 1055 St. Regis Blvd. Dorval, Quebec, Canada H9P 2T4. A first preferred processor is the Matrox Image-LC image processor, which is designed to interface with a wide range of analog and digital devices. The Matrox Image-LC processor, the operator's manual for which is incorporated herein by reference, is a programmable processor that is very versatile, and provides a great many options, such as the ability to perform mathematical computations on a pixel by pixel basis at the processor 84 (as opposed to being performed at the SBC 70). The result is very fast image processing. Because the Image-LC processor is a very capable and fast processor, it is also somewhat expensive and consumes a significant amount of power.

A second preferred processor for use as the image processor 84 is the Matrox IP-8 Frame Grabber. The Matrox IP-8 Frame Grabber, the operator's manual for which is also incorporated herein by reference, is a flexible, low-cost monochrome frame grabber and display processor that offers only a few of the processing features of the Image-LC processor. However, the IP-processor still offers sufficient processing capability for most applications of the present invention. For this reason, and given its lower-cost, and less power consumption, the IP-8 Frame Grabber is the image processor that is generally used most often with the present invention.

The Video Graphics Adapter (VGA) 82 of the control unit 16 comprises a standard VGA board, as is used in any personal computer providing VGA graphics.

The digital controller 80 of the control unit 16 functions to provide an appropriate isolated interface between the control unit 16 and the imager 14 and X-ray source 12 relative to the trigger or synchronization signals that must be sent to the imager 14 and X-ray source 12. More particularly, for the preferred X-ray source 12 and imager 14 described above, the controller 80 produces a TTL (transistor-transistor logic) electronic synchronization signal which when driven to a ground potential accomplishes both (1) the firing of the X-ray source 12, and (2) the integration of the image signal at each pixel site within the imager 14. When the TTL signal is returned to +5 VDC, the X-ray source is inhibited, and the integrated signal is read out of the imager 14 after the next video vertical interrupt. The net result (and desired goal) is that the rapid read out of the video signal from the imager 14 is properly synchronized with the digitizer of the image processor 84.

As seen in FIGS. 1, 2 and 4, the X-ray source 12 is connected to the control unit 16 through the imager 14. That is, the long cable 18 is connected between the control unit 16 and the imager 14, and the short cable 20 is connected between the imager 14 and the X-ray source 12, and there is not direct cable connection between the control unit 16 and the X-ray source 12. An isolation relay is used at the imager 14 to apply a trigger (or "fire") signal to the X-ray source 12 through the short cable 20 as soon as the TTL synchronization signal is pulled low (or no longer than one frame time thereafter, where one frame time is, e.g., the vertical blank interrupt period, typically $\frac{1}{60}$ of a second). The X-ray source continues generating its burst of X-ray pulses until the TTL signal goes high (or until no longer than one frame time after the TTL returns to +5 VDC). Advantageously, use of the isolation relay keeps electrical noise from getting into the video signal or affecting the stored image on the CCD chip. Thus, it is seen that the imager 14 is enabled (its "shutter" is open to receive an image) at the same time as, or perhaps even just slightly before, the X-ray source 12 provides its burst of X-ray pulses, and remains enabled for so long as, or perhaps even just slightly longer than, the burst of X-ray pulses ends. After completion of the exposure, i.e., within one frame time thereafter, the integrated signal acquired at the imager 14 is downloaded to the image processor 84, and is thereafter available for display at the active matrix display 28 and/or for storage within any of the available storage media used by the control unit 16.

Advantageously, because the control unit 16 is based on a PC-type digital computer, and because of the conventional components used within such computer, both in terms of hardware and software, it is capable of accomplishing a wide variety of image acquisition, manipulation and data storage tasks. Many of these tasks may take advantage of recent advances in Graphical User Interface (GUI) technology, particularly in view of the fact that the familiar MICROSOFT (MS) Windows operating system is being used. For example, with hardware which supports "Digital Chromokeying", it is possible to superimpose images stored in the memory of the image acquisition memory buffer with the MS Windows desktop display. Such capability provides a very compact and convenient user interface.

Further, because PC-based technology is used within the control unit 16, there exists great flexibility in how the resulting data is stored and transmitted. For example, the conventional TIF binary file format, commonly used for faxes, drawings, and other graphical (digitized) displays/images in the PC-based environment, may be used to store and manage the digitized images. Fortunately, a significant body of commercially-available software exists to aid in the handling, storage, and management of such displays. In addition, such TIF images can be copied to a standard 1.44

MB floppy diskette, using the floppy disk drive included as part of the control unit 16, or to a standard removable hard drive (which has the capacity to store hundreds of such images) using the PCMCIA port, or transmitted via the modem 36. As a result, the images can be transported, transferred and/or copied onto any other PC compatible system. Such images can then be viewed, manipulated, and/or printed using one of the numerous graphics and desktop imaging programs which are commercially available.

The control unit 16 stores the digital image in a frame buffer memory that forms part of the image processor 84 (FIG. 4). Such storage of the image allows the host computer, i.e., the SBC 70, and/or the image processor 84 (if the image processor has such capability) to perform mathematical calculations, on a pixel-by-pixel basis, in order to enhance and emphasize particular details in the X-ray image. When the image processor 84 has the capability to perform such calculations, as does, e.g., the Matrox Image-LC processor board referenced previously, then such pixel-by-pixel calculations can be completed very rapidly. When the image processor 84 lacks this capability, as does, e.g., the Matrox IP-8, the calculations can still be performed by the SBC 70, but they are not completed near as quickly.

Among the types of mathematical calculations that may be performed on a pixel-by-pixel basis are various convolution techniques, accessible through commercially-available software, that modify the displayed image to produce a variety of effects. These effects include: (1) fine sharpening, which subtly increases the clarity of an image by enhancing high frequency components, making edges of objects appear sharper; (2) coarse sharpening, which is a variation of fine sharpening, but which produces a more dramatic noticeable sharpening; (3) smoothing, which reduces the "grainy" appearance of an image having excessive high frequency noise; (4) horizontal edge detection, which suppresses (i.e., turns black) all pixels in an image except for those which form horizontal edges of objects in the image, thereby causing such horizontal edges to appear white, and making them stand out in high relief; and (5) vertical edge detection, which does the same thing to vertical edges that the horizontal edge detect does to horizontal edges.

It is noted that other mathematical operations and functions could also be used in addition to, or in lieu of, the above listed convolution techniques in order to sharpen and enhance a given image. For example, multiple image arithmetic calculation functions, (i.e., pixel-to-pixel Addition, Subtraction, Multiplication, Division, And, Or, Xor, etc.), Blob Analysis, Pattern Analysis, Fast Fourier Transforms, and other more extensive convolution techniques, could be performed.

Moreover, in addition to mathematical manipulation, the control unit 16 permits a wide variety of display flexibility, which also enhances the desired details of an acquired image. For example, zooming by factors of 2 and 4 are supported, allowing small details to be magnified and viewed in greater detail. Panning and scrolling functions are also available in conjunction with the zoom capability to allow a user to move about within the magnified image. A contrast stretch function, discussed in more detail below, is further provided which interactively allows the user to change the displayed contrast and brightness of specific grayscale regions of the image. Such contrast stretch function is particularly useful for increasing the brightness and clarity of very dense objects.

An invert function is likewise provided within the control unit 167 which changes the image from a black-to-white "positive" image into a white-to-black "negative" image. Such function aids radiographers who are more comfortable viewing images as they would appear, e.g., on X-ray film.

As indicated, the control unit 16 preferably operates in a Windows-based mode, thereby providing an operator of the system, once the system has been set up and turned on, the ability to select various options related to the imaging task at hand. Such options are controlled by appropriate applications software that is stored on the unit's internal hard drive.

Figure 7:
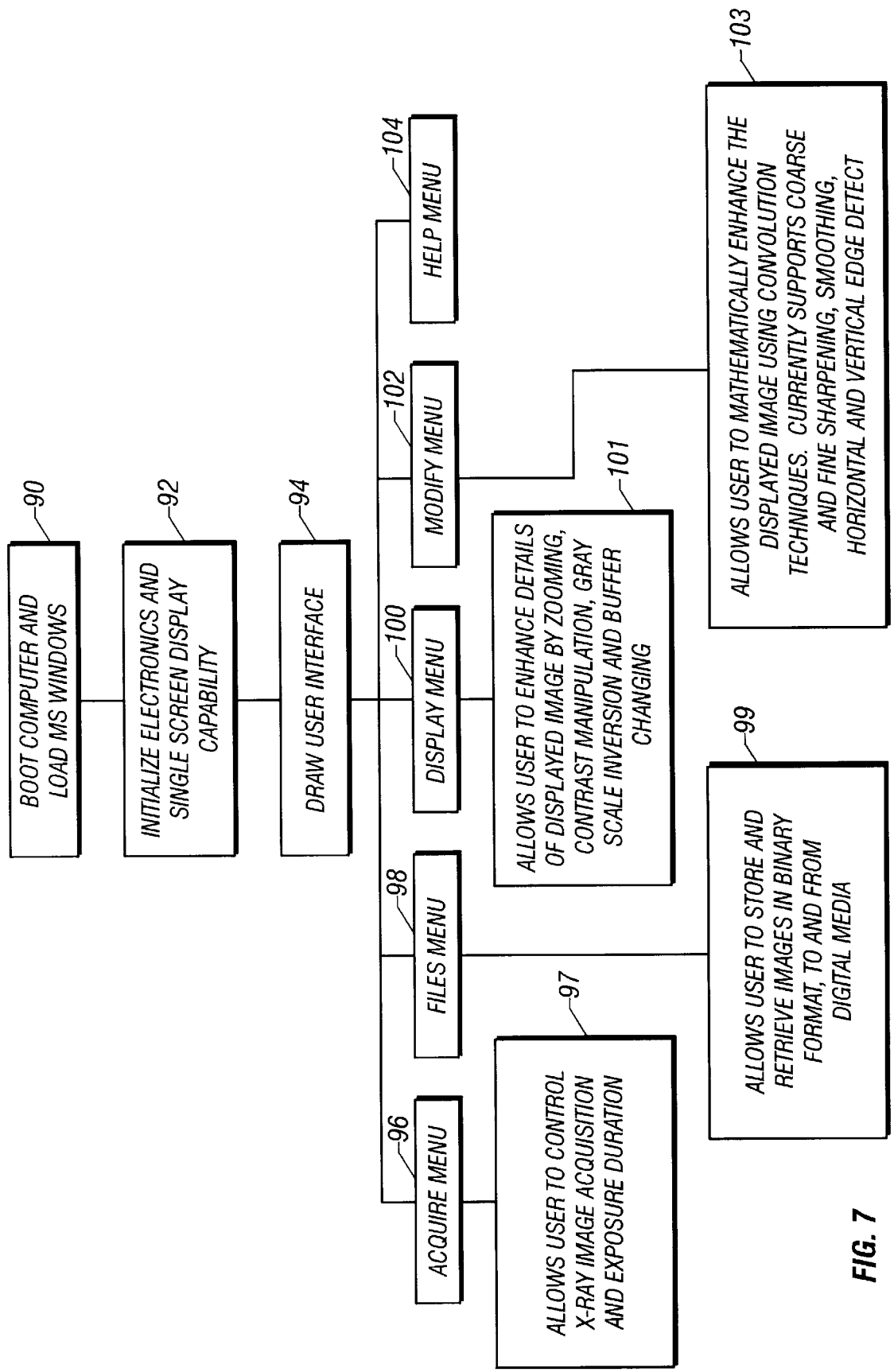
FIG. 7 depicts the various software modules that may be invoked by a user of the imaging system of FIGS. 1 and 2.

A flow diagram of the software control used within the unit 16 is illustrated in FIG. 7. As seen in FIG. 7, when power is first applied to the unit, the computer is booted on and Microsoft Windows is loaded (block 90, FIG. 7). The electronics of the image processor 84 are then initialized, power-on diagnostics are performed, and the single screen display capability is verified (block 92). Once initialized, a User Interface Main Menu is drawn on the screen (block 94) using a conventional windows format.

The User Interface Main Menu screen allows the user to select one of five options. A first option (block 96, FIG. 7) allows the user to get ready to acquire an image. Such option (as indicated at block 97) provides the user with an acquire menu that allows the user to control the X-ray image acquisition and exposure duration. Further details associated with the selection of the "Acquire" option are presented below.

A second option (block 98) provides the user with a "files" menu. The files menu allows the user to store and retrieve images in binary format to and from digital media (block 99), e.g., an internal hard drive, a floppy disk, or a removable hard drive.

A third option (block 100) provides the user with a "display" menu. The display menu allows the user to enhance details of the displayed image (block 101) by, e.g., zooming, contrast manipulation, grayscale inversion, and buffer changing.

A forth option (block 102) provides the user with a "modify" menu. The modify menu allows the user to mathematically enhance the displayed image (block 103) using convolution techniques. Such mathematical enhancements include, at the present time, coarse and fine sharpening, smoothing, and marking horizontal and vertical edge detection.

A fifth option (block 104) provides the user with a "help" menu. The "help" menu provides the user with whatever information may be helpful to the user, e.g., a further description of the other options, the latest enhancements that have been included in the software, and/or any other information that helps the user debug any problems he/she may be experiencing with the operation of the system 10.

Figure 8A:
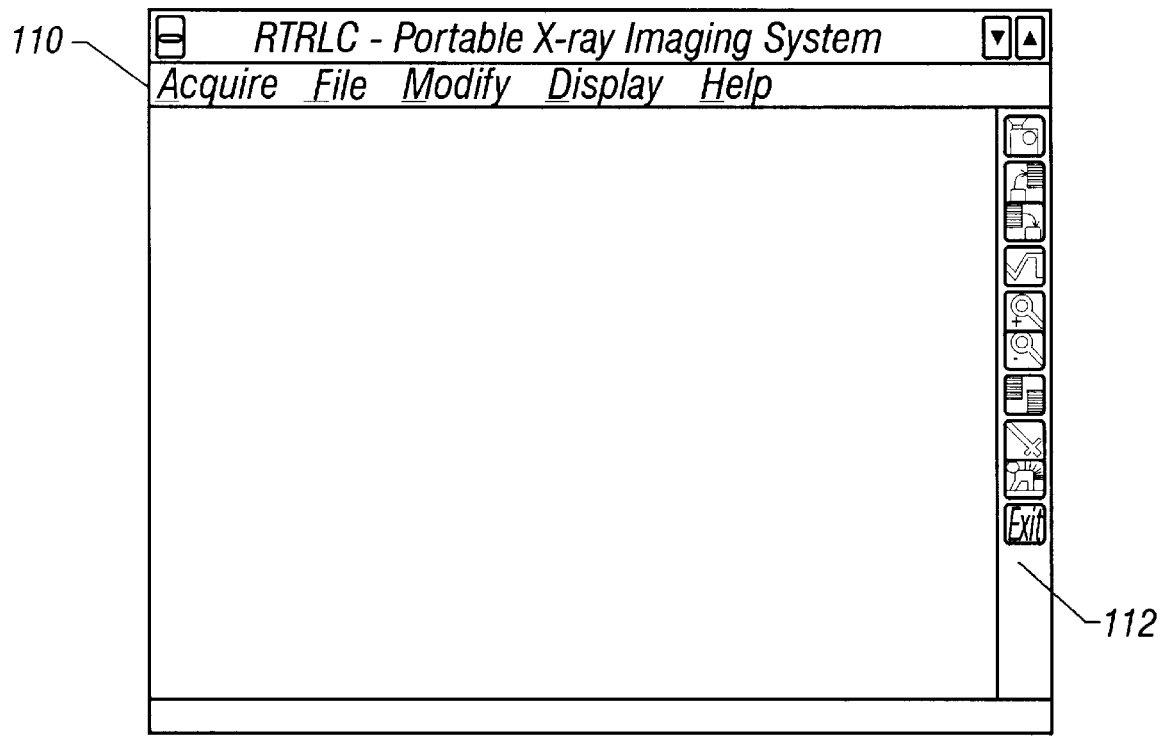
FIGS. 8A, 8B and 8C respectively depict various windows or "screens" that are displayed to a user as different control options are selected.

A representation of the User Interface Main Menu is presented in FIG. 8A. This menu is displayed on the display screen 28. Note that the Main Menu appears as a conventional "window" for use within a Microsoft windows environment. There is a menu bar 110 located across the top of the screen, and a column of icons 112 located on the right of the screen. From this main Windows menu, the user can access the various options provided by pull-down menus or icons associated with each option. The functions which can be activated by the icons are a subset of the functions which can be accessed through the pull-down menus.

As with any Windows environment, selection and activation and/or initialization of each of the various activities represented by the corresponding icons or pull-down menu options is made using the arrow cursor displayed on the flat panel display, or by using keyboard selections consistent with the standard Windows applications. That is, a function represented by an icon is activated, e.g., by simply moving the arrow cursor to the point within the appropriate icon using the mouse (or other pointer device) and pressing (or "clicking") the left button on the mouse, or moving the arrow cursor to the named menu item on the menu bar and pressing the left mouse button. Alternatively, the "Alt" key may be pressed simultaneously with the first (or underlined) letter of the named menu item on the menu bar.

Figure 8B:
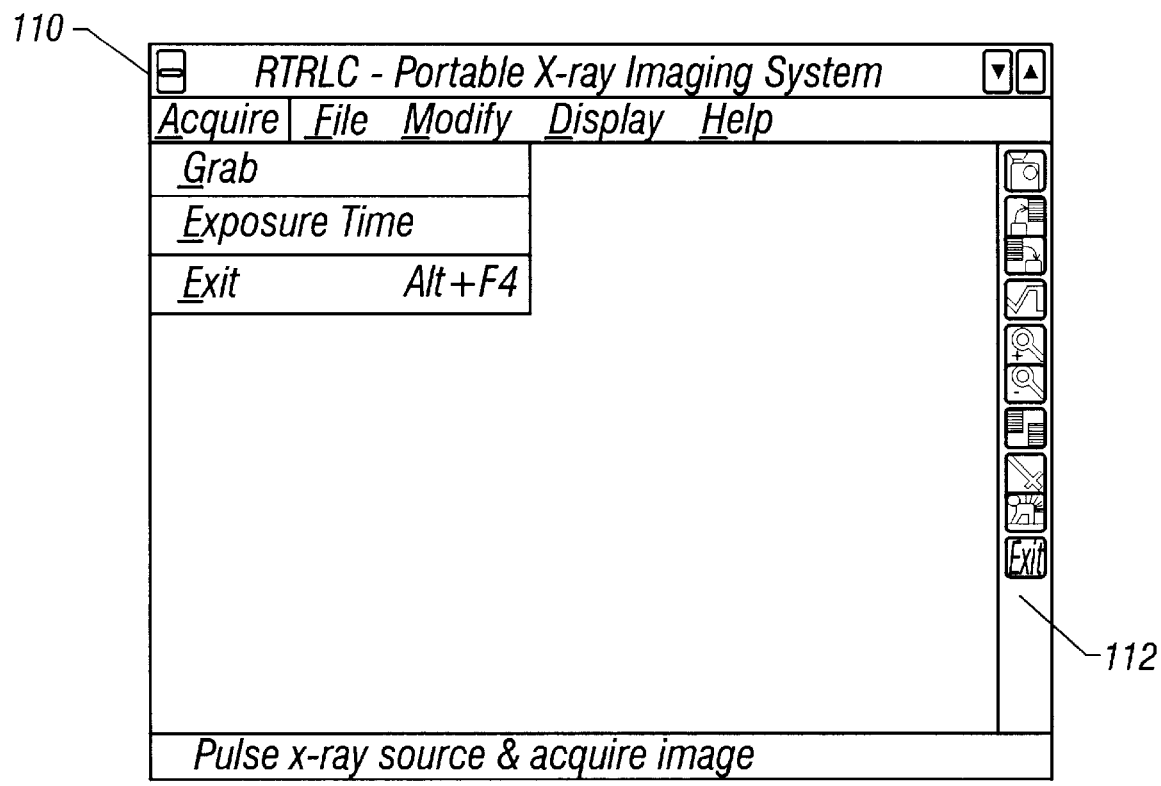

To illustrate, an X-ray image is acquired by moving the arrow cursor and pointing-and-clicking on the Acquire option on the menu bar 110, or equivalent icon in the icon column 112. Such action causes the Acquire pull-down menu to be activated, as represented in FIG. 8B. The Acquire pull-down menu lists three options, as shown in FIG. 8B, including "Grab", "Exposure Time", and "Exit". An image acquisition is referred to as a "grab" because it entails pulsing the X-ray source 12 and "grabbing" the video data resulting therefrom which make up the radioscopic image.

Figure 8C:
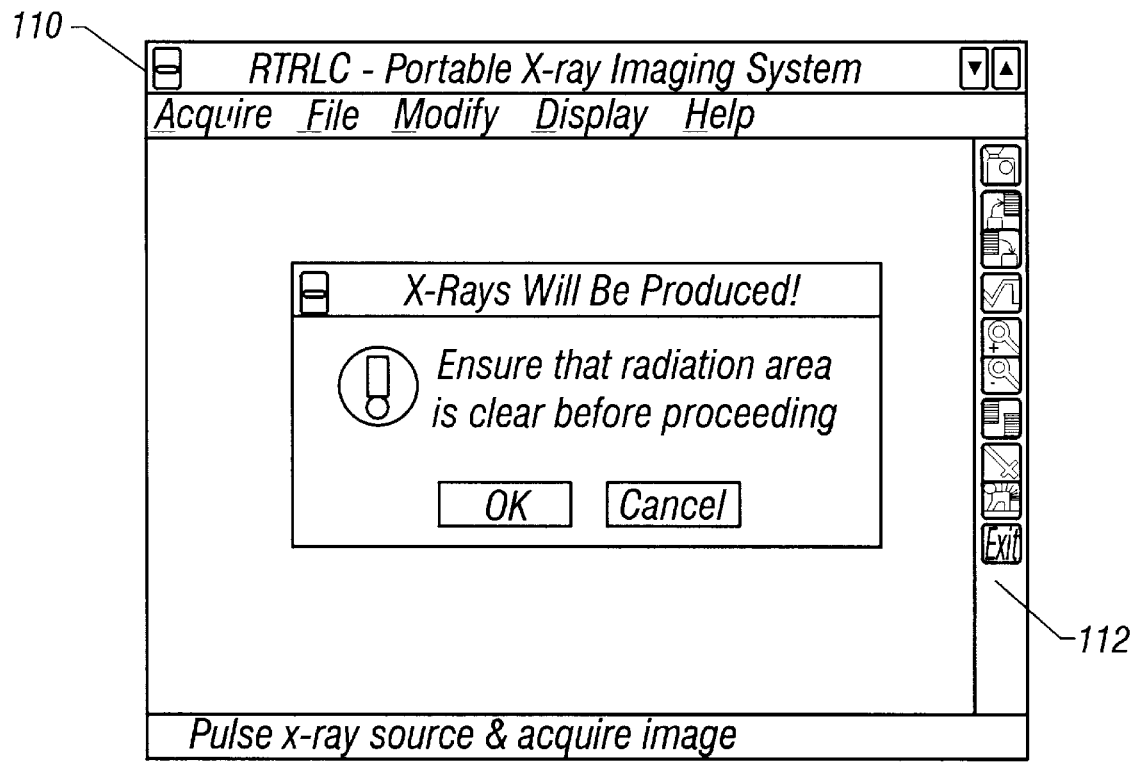

Once the Grab option has been activated, a dialog box appears in the center of the Display Panel as shown in FIG. 8C. This dialog box serves as a safety feature, or software interlock, that warns the operator that X-ray production will be initiated by the next step, and that the X-ray beam area should be clear of all personnel.

As seen in FIG. 8C, two options are provided below the warning: (1) to produce X-rays and acquire an image, the user must use the mouse to point-and-click on the OK button; or (2) the grab request can be cancelled by using the mouse to point-and-click on the Cancel button, which returns the user to the Acquire pull-down menu (FIG. 8B). When the user selects the OK option, the X-ray source pulses immediately and an image forms on the display panel 28. This image is the radioscopic image that is created by having X-rays directed at and pass through the object 22, as sensed by the imager 14, and processed by the circuitry within the control unit 16. Advantageously, at the completion of the Grab sequence, the system returns to the Acquire pull-down menu, and the acquired radioscopic image is displayed beneath the menu overlay graphics.

As mentioned previously, there is an interlock key 24 located on the control panel of the control unit 16, and another interlock key 26 located on the X-ray source. These interlock keys are intended to enhance radiation safety. Both of these keys must be in place and turned to the ON position in order for X-ray production to occur. If either of these keys is not in place and in the ON position, the X-ray source will not fire, a call to the Grab function will time-out, and the system will return to the Acquire pull-down menu without creating a radioscopic image.

Once an image has been acquired, the user may select other menu bar or icon bar options depending on what is to be done next. If the acquired image is not quite right, e.g., due to under or over exposure, or the feature(s) of interest in the image are not properly oriented for definitive evaluation, another image may be acquired after appropriate adjustments are made to the image acquisition time. Such adjustments are made using the Exposure option in the Acquisition pull-down menu, or by adjusting the X-ray source/target/imager geometry. If the quality of the image just acquired is satisfactory, the image can be stored to hard disk or floppy disk using the options found in the File pull-down menu. Further, an acquired image can be visually manipulated using the functions found in the Enhance or Modify pull-down menus. For example, an image which has just been acquired will usually benefit from the Sharp 1 or Sharp 2 enhancements presently offered as the first and second options, respectively, in the Modify menu. These edge sharpening options use the image processors capabilities to make the acquired image appear sharper than the original image. It is to be emphasized, of course, that the use of such edge sharpening options are meant to be exemplary, not limiting.

One particular image enhancement feature of note is the Contrast Stretch option available through the Display pull-down menu. The Contrast Stretch option of the Display menu is used to change the grayscale level distribution of the displayed radioscopic image to facilitate visualization and evaluation by the operator of features of particular interest. This Contrast Stretch option is a particularly valuable option for the present invention due to the large range of grayscale resolution that is available with the display 28. As indicated previously, the display 28 preferably includes the capability of providing 256 different levels or shades of gray, ranging from black to white, within the displayed image. For example, a pure black pixel is represented by a gray scale of 0, while a pure white pixel is represented by a gray scale of 255.

A mapping function is used to map a given intensity (e.g., number of X-ray pulses received at a given pixel site) to a given grayscale value. Thus, for example, a pixel value of 0 (black) means that no radiation was sensed at the given pixel, whereas a pixel value of 255 (white) indicates that a maximum radiation level was sensed at the pixel site.

In the preferred embodiment, the mapping function that relates the sensed intensity of a given pixel site to a specified grayscale value is linear. It is to be emphasized, however, that the mapping function need not be linear, but can be any value. Performing a Contrast Stretch function changes the "slope" and "offset" of the mapping function. Slope and offset are best understood with reference to FIG. 9.

Figure 9:
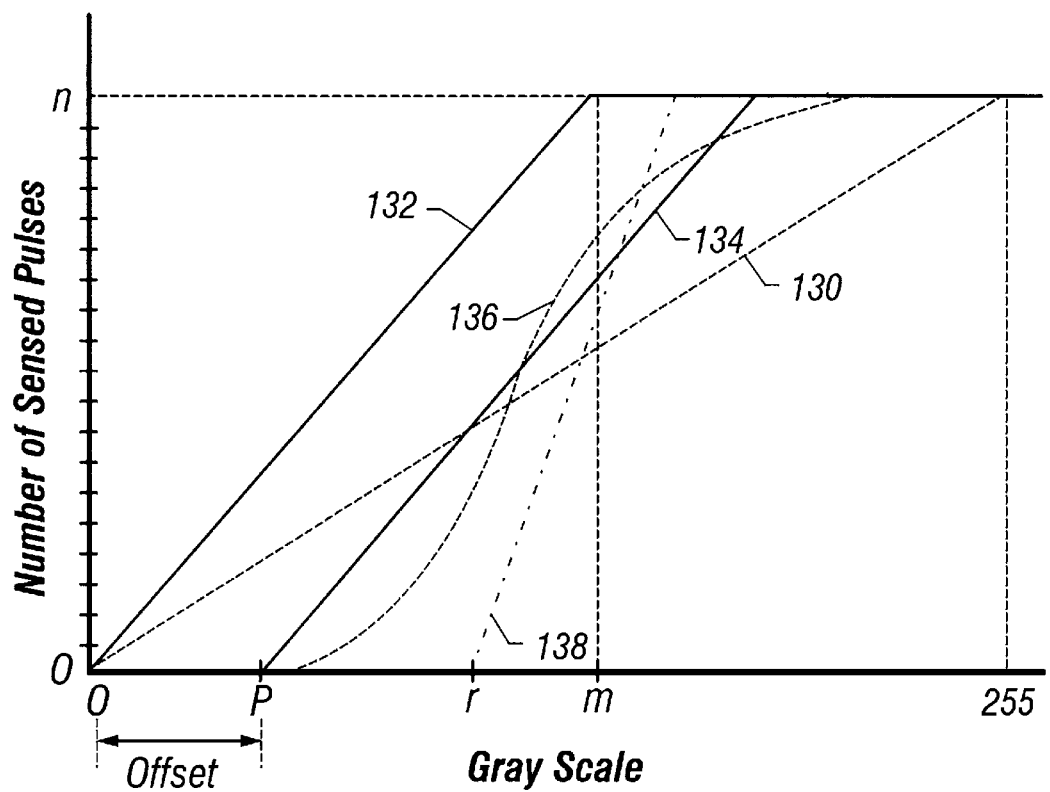
FIG. 9 graphically illustrates the manner in which the present invention achieves contrast stretching.

FIG. 9 depicts a graph that illustrates representative mapping functions that may be used to map the number of sensed pulses at a given pixel site (vertical axis) to a grayscale value (horizontal axis). Thus, for example, the dashed line 130 represents a linear mapping function with no offset and with a slope of n/255, where n represents a specified maximum number of pulses that can be sensed. The solid line 132 in FIG. 9 represents a mapping function with no offset, and having a slope of n/m where m is about ½ of 255. The slope of line 132 is thus about twice that of the line 130. Solid line 134 has a slope that is about the same as that of line 132, but with an "offset" of p, where p is an integer that is about ⅖ of m. The offset thus defines the location within the pixel value range where the linear (or nonlinear) ramp begins. The dashed line 136, for example, defines a ramp that has the same offset p as the line 134, but is not linear. Rather, the line 136 has a general "S" shape, and thus has a varying slope that is the steepest in the mid range of the number of sensed pulses. The dashed-dotted line 138 has an offset of r and a slope that is the steepest of all the lines shown in FIG. 9.

The present invention thus allows the offset and slope of the displayed image to be readily defined using, e.g., the Contrast Stretch function, thereby allowing the quality of the displayed image to be improved. In its present configuration, the Contrast Stretch option acts only on the output to the display panel 28. When images are stored to disk and subsequently retrieved, they will not be stretched as displayed prior to archiving. That is, saving an image to hard or floppy disk stores the data in the display memory buffer, but not the video output parameters. Nonetheless, storing and saving the video output parameters, as well as the image, is something that could be done by those of skill in the art if needed and/or desired.

The image enhancement tools described herein are realized using commercially available imaging application development software. Such software may be obtained, e.g., from Matrox Electronic Systems, Ltd., of Quebec, Canada. Matrox provides, e.g., numerous software programs, including a Windows Utility, that allows a user to load, grab, create, duplicate, save, transmit, display, overlay, and/or process digital images. All of the enhancement features, such as course and fine sharpening, smoothing, horizontal and vertical edge detection, grayscale inversion, contrast stretching, zooming, and buffer changing, are supported by software programs and/or hardware that are commercially available from companies such as Matrox, or other companies like Matrox, e.g., Data Translation, Inc., 100 Locke Drive, Marlboro, Mass. 01752-1192.

As described above, it is thus seen that the present invention provides a high-resolution, solid-state imaging system that utilizes on-chip light integration, thereby eliminating the need for intensifying electro-optic components, and wherein the system is based on a personal-computer controller that facilitates the acquiring, displaying, storing, enhancement, and/or transmitting of a digital image obtained with the system. Advantageously, such system is self-contained, lightweight and portable, and can easily be taken on-site to inspect whatever objects need to be examined without having to move such objects. Once an image is acquired, the image can be immediately sent as digital data over a modem, provided as part of the system, or stored on a floppy disk, or removable hard disk, to facilitate its transfer to an off-site location where the image can be faithfully reproduced for further analysis by off-site experts.

An additional preferred embodiment describes as follows, provides for the propagation of visible light from the X-ray converting screen 42 outwardly from each point 154 impinged by X-ray radiation 152, so as to increase the fraction of light 154 directed towards the CCD camera objective lens 46, while simultaneously reducing the amount of scattered visible light.

Figure 10:
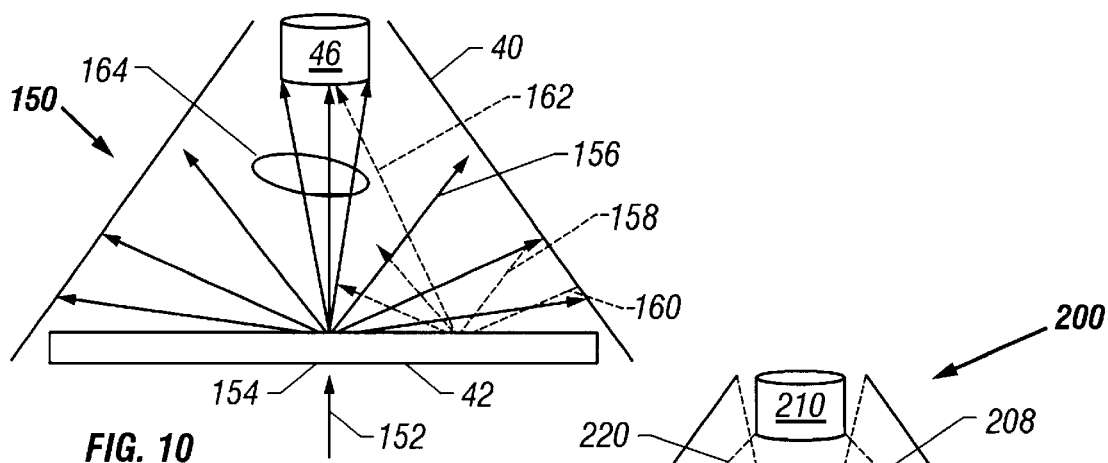
FIG. 10 illustrates the basic emission of light from a diffuse phosphor screen without transmissive films as is employed in the embodiment of FIG. 3A.

FIG. 10 illustrates the basic emission of light from the diffuse phosphor screen 42 without transmissive films as is employed in the embodiment of FIG. 3A discussed above in the mirror folded approach used with the described embodiments. Herein, the phosphor screen 42 converts the impinging X-ray radiation 152 to visible light such that each point 154 impinged on the phosphor screen 42 by X-ray radiation 152 scintillates visible light emissions 156 diverging from the phosphor screen 42.

The light emission in FIG. 10 show an incident 180 degree cone of illumination, from which diverging emissions 156 may reflect off the metal housing 40. Light emissions 158 may then cause scattered light 160, 162 which may result in degraded contrast and image resolution. With the wide cone of illumination of FIG. 10, only a fraction of generated light 164 is collected at the lens 46 of the CCD camera. Generally, one tries to make the walls 40 of the system 150 physically distant from the beam and coat wall 40 surfaces with non-reflective material. However, with the mirror folded optical systems used herein, such approaches are complicated to employ. Moreover, if one wants to restrict the depth of the optical system by using a mirror angle of 45 degrees or greater, the problem of limiting the light emitted 156 and keeping light 158 from reflecting back onto the diffuse phosphor surface where they may now bounce back into the collected beam 162 is very difficult.

To this end, the restriction and focusing of light directly on the surface of the phosphor screen 42 using thin light directing films or structures presents an attractive approach to improve contrast and brightness of radiographic systems which use lenses coupled with X-ray conversion screens. Depending whether the light directing material uses simple masking of emission angles or employs the refraction of an array of lenslets or linear microprisms, the method can effectively concentrate the emission angle of the normal lambertian pattern and redirect the centroid of that angular distribution toward a common point, for example, the center of the collecting lens. In effect, the method trades off an increase in brightness and reduction in off axis emission for the spatial quantification of the totality of light emitted.

Figure 11:
FIG. 11 illustrates a radiographic system utilizing a transmissive film emission modification device such as a microlens film in accordance with the present invention.

The improved system 200 of FIG. 11 represents a radiographic system utilizing transmissive films as an emission modification device for generally focusing the diverging visible light as a restricted cone of illumination. Herein, the radiographic system 200 utilizes a transmissive film emission modification device or lens 202 such as a microlens film. The improved X-ray converter screen 202 includes a substrate 206 converting impinging X-ray 152 radiation to visible light, each point 154 impinged on the substrate 206 thus scintillates visible light emissions. An image sensor CCD camera is configured to sense the visible light using a first lens 210 operable for spatially sensing the visible light within a collection cone 220 directed outwardly. A second lens 204 is provided as a transmissive film through which the visible light emitted from the substrate 206 is transmitted. The second lens 204 is positioned in an optical path between the first lens 210 and the substrate 206 for generally focusing the diverging visible light as a restricted cone of illumination 208 propagating outwardly from each point 154 impinged to increase the fraction of light directed into the collection cone 220 of the first lens 210 while reducing the amount of scattered visible light from said screen.

The lens 210 is provided as an aspherical lens for using a large aperture without developing aberrations and loss of sharpness; an F/0.8 aperture is used with minimal loss of sharpness. The lens 210 used in the described embodiments is made by COMPTAR, Chugai Boyeki (America) Corp., Japan, which has provided satisfactory low light optical performance with a wide aperture, whereas most optical systems tend to suffer serious spherical aberration when wide apertures are employed.

Figure 12:
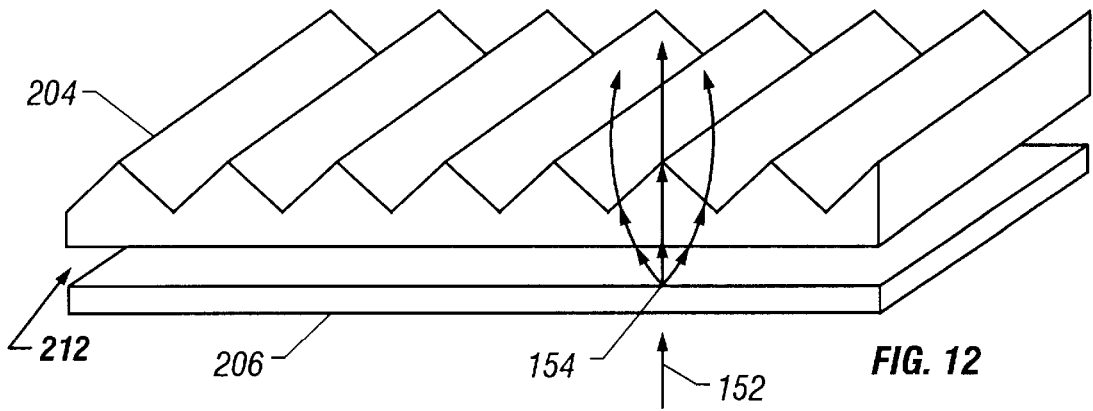
FIG. 12 shows linear prismatic superposed with an X-ray converting screen as is employed in the radiographic system of FIG. 11.

FIG. 12 shows linear prismatic lens 204 superposed with an X-ray converting screen as is employed in the radiographic system of FIG. 11. Depending whether the light directing material uses simple masking of emission angles or employs the refractive of an array of lenslets or linear microprisms, the method can effectively concentrate the emission angle of the normal lambertian pattern and redirect the centroid of that angular distribution toward the enter of the collecting lens. A discrete small optical gap is provided between the phosphor and the optical film to allow the light rays to be refracted in a direction more nearly normal to the emission plane. The screen 204 is then vacuum sealed with the transmissive film 204 with the optical gap provided between said phosphor screen and the transmissive film.

Figure 16:
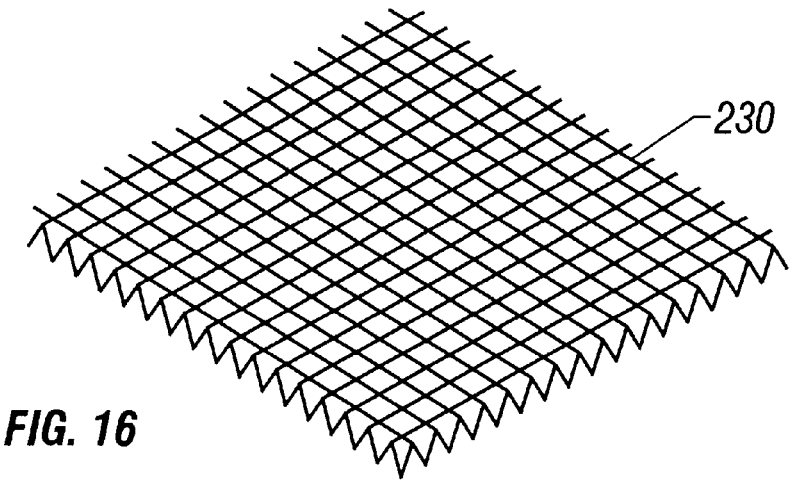
FIG. 16 shows a prismatic film having corrective microlenses or prisms in two dimensions.

As shown in FIG. 12, the enhanced converter screen can be effected using linear structures along a single axis or can be effected using crossed linear structures and one or two dimensional structures to provide enhancement of the optical emission properties in two directions (FIG. 16).

Examples of films which can produce the desired effects are currently produced by 3M Corporation for the purpose of controlling angle of view for computer screens and traffic lights. The 3M materials are referred to as a family of transmissive films known as Brightness Enhancement Film (BEF), and Transmissive Right Angle Film (TRAF). In the described embodiment of FIG. 12, BEF II film from 3M Corp. was used. Herein, limiting the angle of emission and transmitted intensity using chevron-like baffles on the screens surface, refocus it with a sheet of tiny microlens or one or more linear microprism structure which collect a large fraction of the light emitted below their area. Typically the optically active structures have a focal point is very near the screen's surface which allow the light to be highly focused or by proper choice of orientation can also redirect an already restricted emission to incline its center more into the collection cone and away from any other surfaces within the enclosure.

Figure 13:
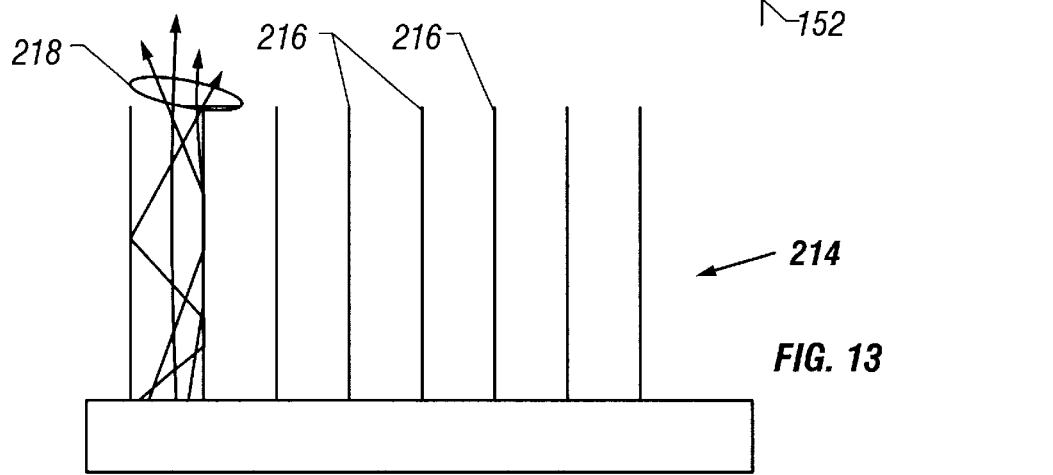
FIG. 13 illustrates transmissive film having a multiplicity of slats which restrict the transmission of light to emissions directed by the orientation of the slats.

FIG. 13 illustrates transmissive film 214 having a multiplicity of slats 216 which restrict the transmission of light to emissions 218 directed by the orientation of the slats with a venetian blind like film wherein an angle restricting baffle is formed from a microscopic distribution of dark slats formed within the film. This is a simple physical restriction of the beam and the angle of emission is limited by the average angle of the slats to the normal, the ratio of slat width to slat pitch and the original distribution of the light from the from the source. The major advantage of this device is that it need not be directly in contact with the phosphor screen to work and that two devices placed in tandem with a 90 degree rotation produce a square emission cone. Since all present films are uniform, this is really a cone of near infinite length since the light comes out at one angle with a rapid fall of in either direction. The limitation of the method is that the light comes off in near parallel rays rather than being focused into the finite cone of the lens and that it throws away all rays that are not initially moving in the proper direction. This limitation can be mitigated by curving the film containing the chevrons so that the light is allowed to come out in a cone focused onto the lens or other optical sensor.

Figure 14:
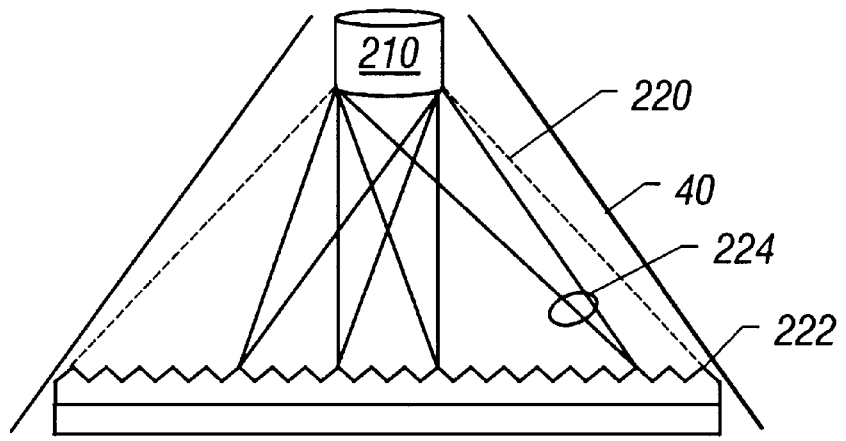
FIG. 14 is a radiographic system showing microlens film focusing the diverging visible light as restricted cones of illumination propagating towards the collection cone of the objective lens in accordance with an additional embodiment of the present invention.

FIG. 14 is a radiographic system showing microlens film focusing the diverging visible light as restricted cones of illumination propagating towards the collection cone of the objective lens 210. The optimal implementation of these films corresponds to a spatially varying film 222 which focuses and bends the light along a one dimensional cone followed by a second layer which does the same for the second axis. Such a film is not currently available but can be approximated by using sections of the fixed angle films and orienting the angles to favor the cone of collection along both axis. A composite structure may be devised from either oriented lenslets of combinations of varying angle microprism arrays which cause the light to be contained within a smaller emission cone, move the central axis of the cone off the perpendicular and toward the lends and provide a smooth reflective surface for any light that does happen to bounce back toward the screen. These films are built in the form of series of repeated long prisms impressed onto a thin resin film. The prisms are adjusted so that any light originating from below is diverted selectively depending on its angle of incidence. Thus, the light intensifying screens can collect light emitted from near their optical focal length and compress the incident 180 degree cone into an out going cone of 30 to 40 degrees in one dimension. Since the source of the light is very near the prism, the resolution is again limited to the pitch of the prism array. Depending on the angle of the prism, the cone can be made narrower and brighter or wider and less intense. Using two films at 90 degrees again provide two dimensional focusing of light but at some loss of resolution since the second grid may not be properly spaced from the source of the original light or simply because its capture angle now includes a larger spot on the surface of the phosphor. Alternative configurations of these films provide prisms with non-symmetric angles 222 which can not only focus the emitted light but also cause its centroid to be bent along a specific angle 224 into the collection cone of the lens 210.

Figure 15:
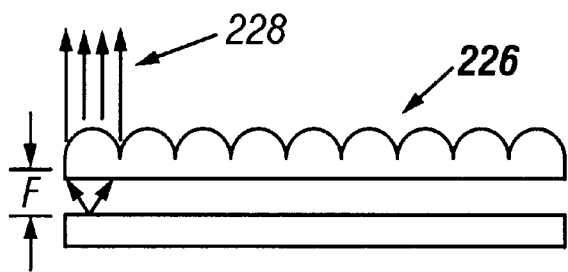
FIG. 15 depicts the operation of transmissive film in the form of multiple corrective microlenses for directing light emissions.

FIG. 15 depicts the operation of transmissive film in the form of multiple corrective microlenses 226 for directing light emissions. Modification of focusing schemes to provide a conical convergence of the orientation of the light beams to further enhance the effectiveness of the light control and to flatten the intensity response 228 when using a wide angle collection lens on the sensor camera. A system using a combination of these films, directly adhered to the phosphor is improved in several ways. First, only light moving in the general direction of the lens is favored with other rays being attenuated, second, light that does escape the collection cone and hits a flat surface returns to hit a smooth surface rather than a diffuse one. The reflection angle is well defined and not likely to be recaptured within the collection cone.

FIG. 16 shows a prismatic film 230 having corrective microlenses or prisms in two dimensions, e.g., using crossed prismatic films for a 2-dimensional focus, or using molded lenslets for 2-dimensional focusing. Thus, the operation of transmissive film in the form of multiple corrective microlenses for directing light emissions.

While the invention herein disclosed has been described by means of specific embodiments and applications thereof, numerous modifications and variations could be made thereto by those skilled in the art without departing from the scope of the invention set forth in the claims.

What is claimed is:

1. An X-ray converter screen, comprising:
    means for converting impinging X-ray radiation to visible light, each point impinged on said converting means by X-ray radiation scintillating visible light emissions diverging from said converting means wherein said converting means comprises a substrate having a generally flat shape made of a scintillating material; and
    means for modifying transmission of visible light emitted from said converting means, said modifying means generally limiting diverging visible light to a restricted cone of illumination propagating outwardly from each point impinged on said converting means by the X-ray radiation wherein a centroid of an angular distribution of each restricted cone of illumination is directed to a common point.

2. An X-ray converter screen, comprising:
    a substrate having a generally flat shape made of a scintillating material for converting impinging X-ray radiation to visible light, each point impinged on said substrate by X-ray radiation scintillating visible light emissions diverging from said substrate; and
    an emission modification layer through which the visible light emitted from said substrate is transmitted, said emission modification layer generally limiting diverging visible light to a restricted cone of illumination propagating outwardly from each point impinged on said substrate by the X-ray radiation wherein a centroid of an annular distribution of each restricted cone of illumination is directed to a common point.

3. An X-ray converter screen as recited in claim 2, wherein said emission modification layer enhances light collection from the visible light converted by said substrate to improve the optical collection efficiency.

4. An X-ray converter screen as recited in claim 2, wherein said emission modification layer comprises light collection lenses for reducing the internal scattering of light provided by said substrate.

5. An X-ray converter screen as recited in claim 2, wherein said emission modification layer is superposed with said substrate.

6. An X-ray converter screen as recited in claim 5, wherein said substrate comprises a phosphor screen made out of deposited crystals of a salt that gives off visible light when impinged upon by X-rays.

7. An X-ray converter screen as recited in claim 6, wherein said emission modification layer comprises a transmissive film for refracting the visible light propagating therethrough.

8. An X-ray converter screen as recited in claim 7, wherein said transmissive film comprises a multiplicity of slats for restricting the transmission of the visible light to emissions directed by the orientation of said slats.

9. An X-ray converter screen as recited in claim 7, wherein said transmissive film comprises a transmissive right angle film.

10. An X-ray converter screen as recited in claim 7, wherein said transmissive film comprises a brightness enhancement film.

11. An X-ray converter screen as recited in claim 10, wherein said phosphor screen is vacuum sealed with said transmissive film.

12. An X-ray converter screen as recited in claim 11, wherein an optical gap is provided between said phosphor screen and said transmissive film.

13. An X-ray converter screen as recited in claim 12, wherein said transmissive film comprises a first chevron-like surface structure having a multiplicity of aligned linear prismatic lenses for concentrating the visible light emitted from said phosphor screen.

14. An X-ray converter screen as recited in claim 13, comprising a second transmissive film comprising a second chevron-like surface structure having a multiplicity of aligned linear prismatic lenses, said transmissive films being superposed with said first and said second chevron-like surface structures being crossed with one another for concentrating the visible light emitted from said phosphor screen in two dimensions.

15. An X-ray converter screen as recited in claim 11, wherein said transmissive film comprises a microlens surface structure having a multiplicity of lenslets for focusing the visible light emitted from said phosphor screen.

16. An X-ray converter screen as recited in claim 15, wherein said microlens surface structure of said transmissive film comprises a multiplicity of spherical lenses.

17. A radiographic system, comprising:

an X-ray converter screen for converting impinging X-ray radiation to visible light wherein said converting means comprises a substrate having a generally flat shape made of a scintillating material, each point impinged on said converter screen by X-ray radiation scintillating visible light emissions diverging from said converter screen;

an image sensor configured to sense the visible light from said screen;

a first lens operable with said image sensor for spatially sensing the visible light within a collection cone directed outwardly from said image sensor; and a second lens through which the visible light emitted from said screen is transmitted, said second lens being positioned in an optical path between said first lens and said screen for generally focusing the diverging visible light as a restricted cone of illumination propagating outwardly from each point impinged on said screen to increase the fraction of light directed into the collection cone of said first lens and reducing the amount of scattered visible light from said screen wherein a centroid of an angular distribution of each restricted cone of illumination is directed to a common point.

18. A radiographic system as recited in claim 17, wherein said X-ray converter and said X-ray sensor are configured for medical applications employing low-voltage imaging.

19. A system as recited in claim 17, wherein said second lens comprises a transmissive film for refracting the visible light propagating therethrough.

20. A system as recited in claim 19, wherein said transmissive film comprises prismatic brightness enhancement film.

21. A system as recited in claim 19, wherein said transmissive film comprises a microlens surface structure having a multiplicity of lenslets for focusing the visible light emitted from said screen.

22. A system as recited in claim 21, wherein said first lens comprises an aspheric lens.

23. A method of converting X-ray radiation to visible light, comprising the steps of:

providing a phosphor screen having a generally flat shape made of a scintillating material for converting impinging X-ray radiation to visible light, each point impinged on the phosphor screen by X-ray radiation scintillating visible light emissions diverging from the phosphor screen; and superposing the phosphor screen with a transmissive film for modifying the transmission of visible light emitted from the phosphor screen to generally limit the diverging visible light to a restricted cone of illumination propagating outwardly from each point impinged on the phosphor screen by the X-ray radiation wherein a centroid of an angular distribution of each restricted cone of illumination is directed to a common point.

24. A method as recited in claim 23, wherein said superposing step comprises the step of superposing a brightness enhancement film.

25. A method as recited in claim 23, comprising the step of vacuum sealing the phosphor screen with the transmissive film.

26. A method as recited in claim 23, comprising the step of providing an optical gap between the phosphor screen and the transmissive film.

* * * * *